(12) United States Patent
Fiering et al.

(10) Patent No.: US 10,946,133 B2
(45) Date of Patent: Mar. 16, 2021

(54) SYSTEMS AND METHODS FOR PARALLEL CHANNEL MICROFLUIDIC SEPARATION

(71) Applicant: The Charles Stark Draper Laboratory, Inc, Cambridge, MA (US)

(72) Inventors: Jason Oliver Fiering, Boston, MA (US); Hoi-Cheong Steve Sun, Tampa, FL (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 0 days.

(21) Appl. No.: 15/962,420

(22) Filed: Apr. 25, 2018

(65) Prior Publication Data

US 2018/0236159 A1 Aug. 23, 2018

Related U.S. Application Data

(63) Continuation-in-part of application No. 14/815,501, filed on Jul. 31, 2015, now Pat. No. 10,099,002.
(Continued)

(51) Int. Cl.
*A61M 1/36* (2006.01)
*B01D 21/28* (2006.01)

(52) U.S. Cl.
CPC .......... *A61M 1/3678* (2014.02); *A61M 1/365* (2014.02); *A61M 2205/3673* (2013.01); *B01D 21/283* (2013.01)

(58) Field of Classification Search
CPC ................ A61M 1/3678; A61M 1/365; A61M 2205/3673; B01D 21/283; B01D 29/115;
(Continued)

(56) References Cited

U.S. PATENT DOCUMENTS 6,929,750 B2 8/2005 Laurell et al.
8,083,068 B2 12/2011 Kaduchak et al.
(Continued)

FOREIGN PATENT DOCUMENTS

EP 0 914 184 A1 5/1999
EP 1 809 399 B1 8/2009
(Continued)

OTHER PUBLICATIONS

International Preliminary Report on Patentability dated Mar. 13, 2014 in PCT Application No. PCT/US2012/052886 (10 pages).
(Continued)

*Primary Examiner* — Cameron J Allen
(74) *Attorney, Agent, or Firm* — Foley & Lardner LLP

(57) ABSTRACT

The present disclosure describes a system and method for microfluidic separation. More particularly, the disclosure describes a system and method for the purification of a fluid by the removal of undesired particles. The device includes microfluidic separation channels that include multiple outlets. The device also includes isolation slots positioned between each of the microfluidic separation channels. The device's base includes multiple acoustic transducers which in some implementations are configured to protrude into the isolation slots. The acoustic transducers are configured to generate aggregation axes within the separation channels, which are used to separate out undesired particles.

20 Claims, 17 Drawing Sheets

Related U.S. Application Data

(60) Provisional application No. 62/489,560, filed on Apr. 25, 2017, provisional application No. 62/031,662, filed on Jul. 31, 2014.

(58) Field of Classification Search
CPC ...... B01D 37/00; B01D 29/52; B01D 29/865; B01D 2201/0415; B01D 2201/0446; B01D 2201/127; B01L 3/502753; B01L 3/502761; B01L 2400/0436; B01L 2200/0652; B01L 2300/0816; B01L 2200/0636; B01L 2200/10; B01L 2300/0864; G01N 33/5044; G01N 2015/142; G01N 33/5005; G01N 33/574
See application file for complete search history.

(56) References Cited

U.S. PATENT DOCUMENTS

| | | | |
|---|---|---|---|
| 10,099,002 B2 | 10/2018 | Sun et al. | |
| 10,166,323 B2* | 1/2019 | Fiering | A61M 1/3693 |
| 2003/0150792 A1 | 8/2003 | Koehler et al. | |
| 2004/0005582 A1 | 1/2004 | Shipwash | |
| 2004/0091398 A1* | 5/2004 | Gilbert | B01D 57/02 |
| | | | 422/504 |
| 2004/0109793 A1 | 6/2004 | McNeely et al. | |
| 2008/0181828 A1 | 7/2008 | Kluck | |
| 2008/0217259 A1 | 9/2008 | Siversson | |
| 2010/0006501 A1 | 1/2010 | Laurell et al. | |
| 2010/0078384 A1 | 4/2010 | Yang | |
| 2011/0250585 A1 | 10/2011 | Ingber et al. | |
| 2013/0043170 A1 | 2/2013 | Rose et al. | |
| 2013/0048565 A1 | 2/2013 | Fiering et al. | |
| 2014/0209542 A1 | 7/2014 | Spain et al. | |
| 2015/0137015 A1* | 5/2015 | Toh | A61M 39/04 |
| | | | 251/149 |
| 2016/0008532 A1 | 1/2016 | Fiering et al. | |
| 2016/0030660 A1 | 2/2016 | Sun et al. | |

FOREIGN PATENT DOCUMENTS

| | | |
|---|---|---|
| EP | 2 145 687 A1 | 1/2010 |
| EP | 2 352 570 A2 | 8/2011 |
| WO | WO-98/46986 | 10/1998 |
| WO | WO-02/12896 | 2/2002 |
| WO | WO-02/29400 | 4/2002 |
| WO | WO-2006/032703 | 3/2006 |
| WO | WO-2006/114596 | 11/2006 |

OTHER PUBLICATIONS

International Preliminary Report on Patentability dated Sep. 11, 2015 in PCT App No. PCT/US2014/022701.
International Search Report and Written Opinion for PCT/US2018/029328 dated Jun. 20, 2018.
International Search Report and Written Opinion in PCT/US2014/022701 dated Jul. 18, 2014.
Non-Final Office Action on U.S. Appl. No. 16/350,217 dated Oct. 3, 2019.
Notice of Allowance on U.S. Appl. No. 14/815,501 dated Jun. 13, 2018.
Office Action on U.S. Appl. No. 14/815,501 dated Feb. 8, 2018.
Requirement for Restriction/Election on U.S. Appl. No. 14/772,216 dated Jul. 21, 2017.
Requirement for Restriction/Election on U.S. Appl. No. 14/815,501 dated Oct. 4, 2017.
U.S. Non Final Office Action on U.S. Appl. No. 13/598,401 dated Jan. 2, 2015.
U.S. Notice of Allowance on U.S. Appl. No. 14/168,822 dated Aug. 3, 2016 (CSDL-221US).
U.S. Office Action in U.S. Appl. No. 13/598,401 dated Jul. 1, 2015.
U.S. Office Action on U.S. Appl. No. 13/598,401 dated May 20, 2016 (CSDL-2146US).
U.S. Office Action on U.S. Appl. No. 14/772,216 dated Dec. 26, 2017.
Notice of Allowance on U.S. Appl. No. 14/772,216 dated Aug. 27, 2018.
Notice of Allowance on U.S. Appl. No. 15/362,068 dated Jan. 26, 2018.
Notice of Allowance on U.S. Appl. No. 16/350,217 dated Jan. 13, 2020.
U.S. Notice of Allowance on U.S. Appl. No. 13/598,401 dated Jun. 2, 2017.
U.S. Office Action on U.S. Appl. No. 13/598,401 dated Jan. 30, 2017.
International Search Report and Written Opinion dated Dec. 11, 2012 in PCT Application No. PCT/US2012/052886.
U.S. Office Action on U.S. Appl. No. 15/362,068 dated Jul. 11, 2017.
U.S. Notice of Allowance on U.S. Appl. No. 15/362,068 dated Jan. 26, 2018.
U.S. Notice of Allowance on U.S. Appl. No. 14/168,822 dated Mar. 7, 2016.
U.S. Notice of Allowance on U.S. Appl. No. 14/168,822 dated Aug. 3, 2016.

* cited by examiner

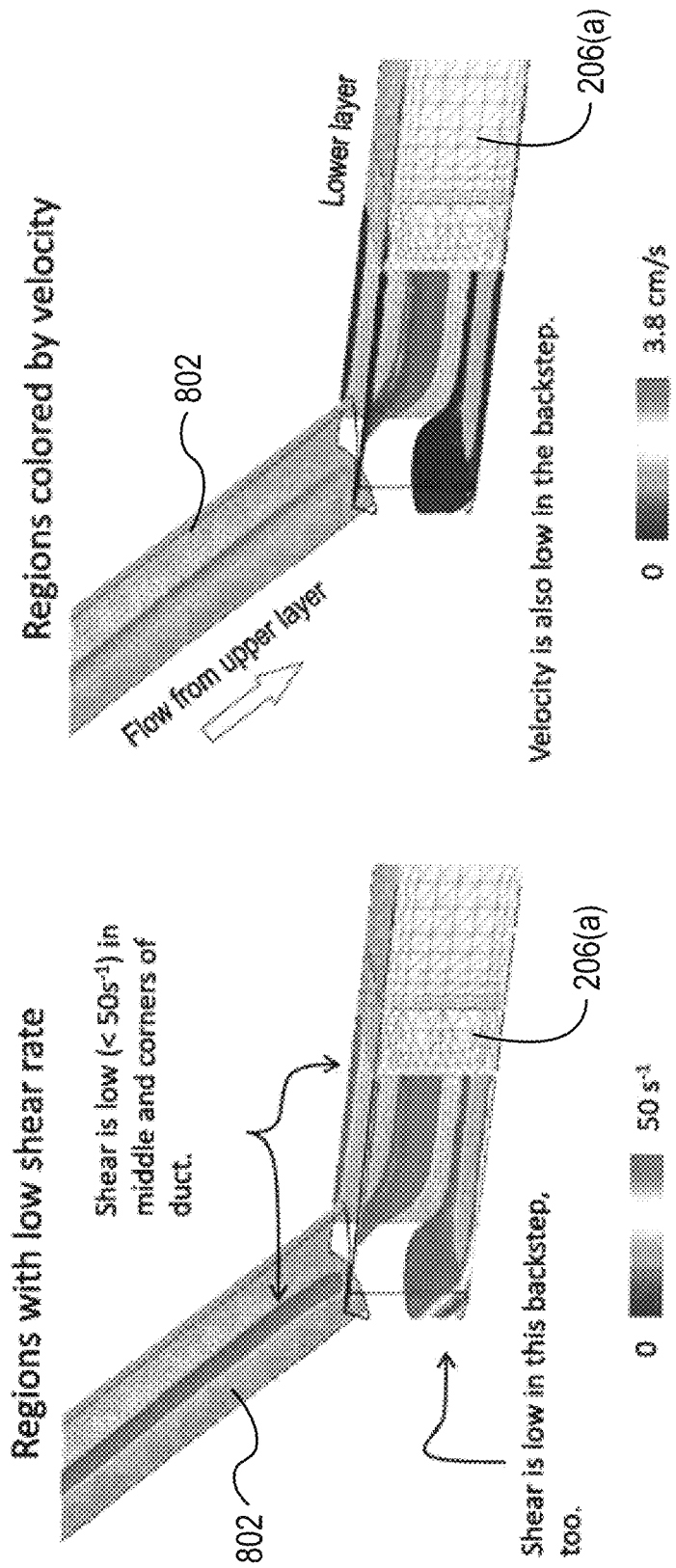

SYSTEMS AND METHODS FOR PARALLEL CHANNEL MICROFLUIDIC SEPARATION

CROSS-REFERENCE TO RELATED APPLICATIONS

The present application claims the benefit of priority under 35 U.S.C. § 120 as a continuation-in-part of U.S. patent application Ser. No. 14/815,501 filed Jul. 31, 2015, which claims the benefit of priority to U.S. Provisional Patent Application No. 62/031,662 filed on Jul. 31, 2014. This application also claims the benefit of priority to U.S. Provisional Patent Application No. 62/489,560, filed Apr. 25, 2017. Each of the foregoing applications are herein incorporated by reference in their entirety.

BACKGROUND

The concept of blood cleansing and separation has been tried previously but remains laborious. Previous blood cleansing concepts have included laboratory scale methods of centrifugation, capillary electrophoresis, liquid chromatography, field flow fractionation, and liquid-liquid extraction. These devices have failed to deliver continuous flow cleansing devices. In addition to often discarding large portions of the blood, current cleansing devices may rely on: diluents, sheath flow, controlled solution conductivity, costly microfabricated on-chip materials, and toxic additives.

Chimeric Antigen Receptor T-cell therapies (CAR-T) can use genetically engineered I-cells re-infused into the patient to recognize and kill cancer cells. The first step can be to isolate the I-cells from a sample of the patient's blood. The blood sample can typically be a 300-400 ml product enriched in white blood cells (leukapheresis), which can still include only about 1% of the target T-cells. The current isolation practice can involve laborious centrifugal separation under highly controlled conditions, which can damage the blood cells.

SUMMARY OF THE DISCLOSURE

The present solution can reduce costs and increase access to life-saving therapy by purifying lymphocytes, including T-cells, from patient blood samples. The present solution can acoustically separate lymphocytes at rates of 2 ml/min or higher. The present solution provides a polystyrene acoustophoretic device that can accept standard leukapheresis product with only 1:1 dilution and is tunable. In a high-recovery mode, the system can recover about 72% of lymphocytes with 90.4% purity. In a high-purity mode, the system can recover about 43% of lymphocytes with a 96.8% purity. The performance of the present device can exceed that achieved by existing centrifugal methods. The present solution can also achieve between about 80% and about 90% red blood cell (RBC) separation at rates between about 0.5 and about 2 mL/min.

As an overview, the multi-channel system can include multiple channels separated by air gaps to substantially prevent acoustic coupling of neighboring channels. The system can also include distribution and collection manifolds that distribute blood from a main inlet to each of the channels and collect the outflow to two outlets. The two collection manifolds to the two outlet can be fabricated on opposing faces of a substrate and connected by holes penetrating the substrate.

According to one aspect of the disclosure a separation device can include a first substrate, a second substrate, and a third substrate. The first substrate can include a first plurality of microfluidic channels that are defined in a first face of the first substrate. Each of the first plurality of microfluidic channels can include an upstream portion and a downstream portion. The second plurality of microfluidic channels can be defined in a second face of the first substrate. Each of the second plurality of microfluidic channels can include an upstream portion and a downstream portion. The first substrate can include a plurality of via channels coupling the downstream portion of the first plurality of microfluidic channels to the upstream portion of the second plurality of microfluidic fluid channels. The second substrate can be coupled with the first face of the first substrate. The second substrate can define a wall of the first plurality of microfluidic fluid channels. The third substrate can be coupled with the second face of the first substrate. The third substrate can define a wall of the second plurality of microfluidic fluid channels. The first, second, or third substrate can be configured to couple with a base substrate comprising one or more acoustic transducers.

The first substrate can include an isolation slot that is positioned between each of the first plurality of microfluidic fluid channels. Each of the one or more acoustic transducers can protrude perpendicular to a face of the base substrate and into the isolation slot positioned between each of the first plurality of microfluidic fluid channels. The isolation slots can be positioned between each of the first plurality of microfluidic fluid channels run substantially parallel to and the entire length of the first plurality of microfluidic channels. The device can also include the base substrate that can include the one or more acoustic transducers. Each of the one or more acoustic transducers can be coupled with the second face (or other free face) of the first substrate.

The downstream portion of the each of the first plurality of microfluidic fluid channels can include a first outlet that is positioned substantially along a longitudinal axis. The downstream portion of the each of the first plurality of microfluidic fluid channels can include a second outlet positioned adjacent to a lateral wall of the first outlet. The first substrate can define a manifold that is configured to distribute a fluid to the first plurality of microfluidic fluid channels. The manifold can include a network of biomimetic channels. A distribution portion of the manifold can be defined in the first face of the first substrate and a collection portion of the manifold can be defined in the first face and the second face of the first substrate.

In some implementations, each of the plurality of microfluidic separation channels also include a first wall that has a first thickness and a second wall opposite the first wall that has a second thickness. In some implementations, the first thickness and the second thickness are equal to $c_s(f)/4f$, or an odd multiple thereof, where $c_s(f)$ is a frequency dependent speed of a shear wave through the plastic.

In other implementations, the second thickness is different than the first thickness. In some implementations, the first thickness is about $c_w/4f+d$, the second thickness is about $c_w/4f-d$, and a lateral width of each of the of microfluidic separation channels is about $c_f/2f$, where $c_w$ is an odd multiple of an acoustic velocity of an acoustic wave in the plastic substrate, $c_f$ is an acoustic velocity of the acoustic wave in a fluid flowing through each of the plurality of microfluidic separation channels, f is an operating frequency of the acoustic wave, and d is a width increment defined by $c_f/16f < d < c_f/4f$.

According to at least one aspect of the disclosure, a method can include providing a fluid cleansing device. The device can include a first substrate, a second substrate, and a third substrate. The first substrate can include a first plurality of microfluidic channels that are defined in a first face of the first substrate. Each of the first plurality of microfluidic channels can include an upstream portion and a downstream portion. The second plurality of microfluidic channels can be defined in a second face of the first substrate. Each of the second plurality of microfluidic channels can include an upstream portion and a downstream portion. The first substrate can include a plurality of via channels coupling the downstream portion of the first plurality of microfluidic channels to the upstream portion of the second plurality of microfluidic fluid channels. The second substrate can be coupled with the first face of the first substrate. The second substrate can define a wall of the first plurality of microfluidic fluid channels. The third substrate can be coupled with the second face of the first substrate. The third substrate can define a wall of the second plurality of microfluidic fluid channels. The first, second, or third substrate can be configured to couple with a base substrate comprising one or more acoustic transducers. The method can include flowing a fluid that includes particles through the first plurality of microfluidic channels. The method can include directing, with an acoustic wave generated by the one or more acoustic transducers, the particles to a first aggregation axis of each of the first plurality of microfluidic channels.

The method can include flowing the fluid through a manifold defined in the first substrate. The manifold can include a network of biomimetic channels. The method can include flowing the fluid through a distribution portion of the manifold that is defined in the first face of the first substrate. The method can include collecting at least a portion of the fluid at a collection portion of the manifold defined in the first face and the second face of the first substrate. The first substrate can include an isolation slot positioned between each of the first plurality of microfluidic fluid channels. Each of the one or more acoustic transducers can protrude perpendicular to a face of the base substrate and into the isolation slot positioned between each of the first plurality of microfluidic fluid channels. One or more acoustic transducers can extend laterally along the base substrate and parallel to the first substrate.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIG. 9 illustrates the wall shear rates experienced in the transition between via channels and the collection channel.

FIG. 10 illustrates the fluid velocity experienced in the transition between the via channels and the collection channel.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Figure 1:
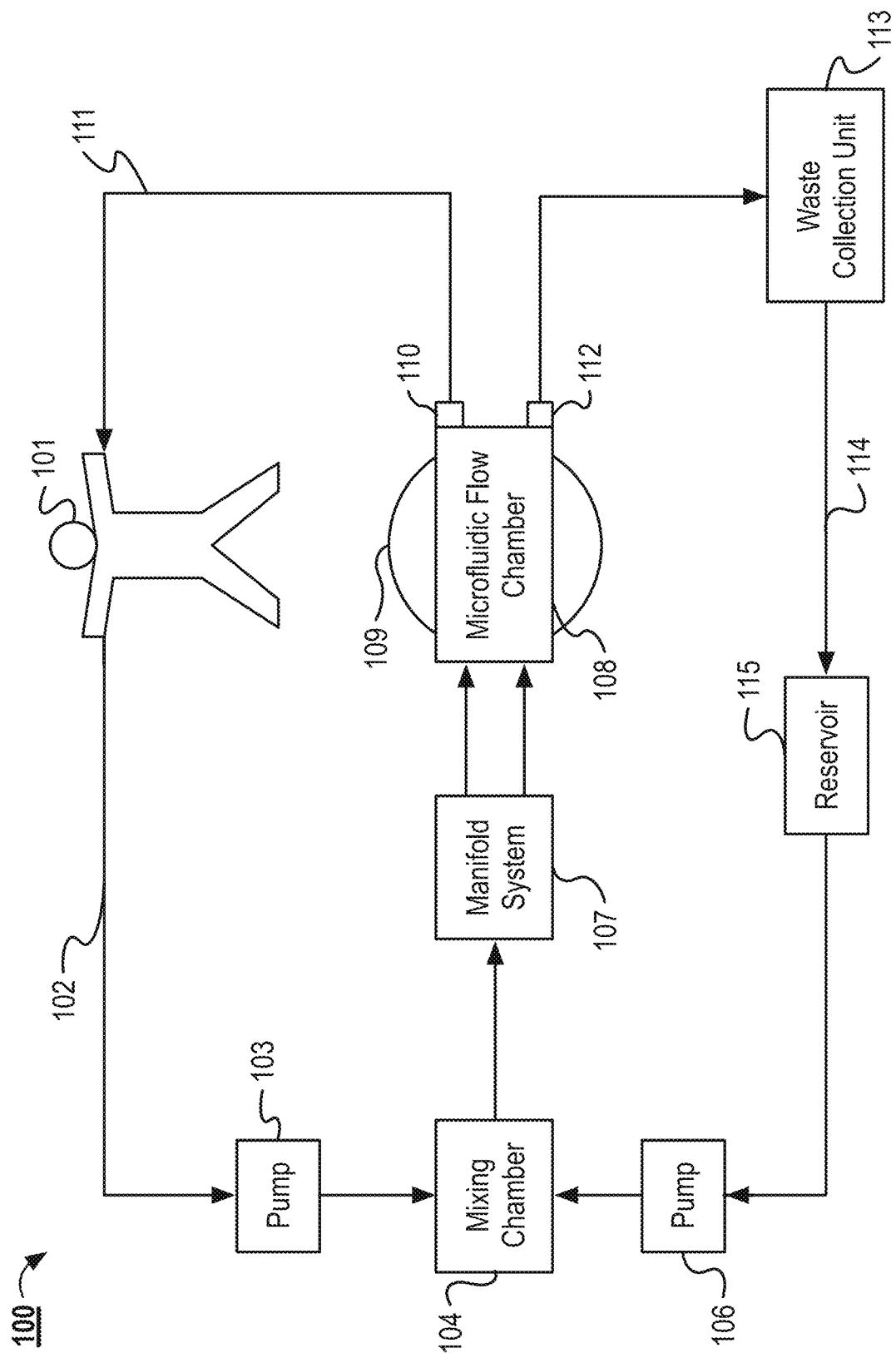
FIG. 1 illustrates an example system for separating contents of a fluid.

FIG. 1 illustrates an example system 100 for separating the contents of a fluid. In the system 100, blood (or another fluid to be processed) is removed from a patient 101 via an intravenous line 102. The blood is then pumped to a mixing chamber 104 by a pump 103. In the mixing chamber 104, capture particles are mixed with the blood. The components of the capture particles are stored in a reservoir 115. From the reservoir 115, the capture particles are pumped by a pump 106 into the mixing chamber. From the mixing chamber 104, the blood and capture particles enter a manifold system 107. The manifold system 107 distributes the blood and capture particles to a plurality of separation channels contained within the microfluidic flow chamber 108. The microfluidic flow chamber 108 includes one or more piezoelectric acoustic transducers 109. The acoustic waves generated by the acoustic transducers 109 are used to funnel the contents of the blood and capture particles to specific outlets of the separation channels. In some implementations, the patient 101 can be replaced with fluid reservoir or tank. For example, the patient's blood can be pre-drawn from the patient 101 and then processed by the system 100 at a later time. In another example, the system 100 can be used to separate the components from a fluid other than blood and the fluid can be stored in a reservoir and be processed with the system 100.

As the blood flows through the microfluidic flow chamber 108, the cleansed blood flows to a first outlet 110. After exiting the first outlet 110, the blood returns to the patient 101, via a second intravenous line 111. The capture particles and other waste material removed from the blood exit the microfluidic flow chamber 108 via a second outlet 112. The waste material and capture particles enter a waste collection unit 113. In the waste collection unit 113, the capture particles are separated from the waste material. Once separated, the waste material is discarded and the capture particles are returned to the reservoir 115 by tubing 114. Once returned to the reservoir 115, the capture particles are reused in the system to remove additional waste material from whole blood as it continues to flow through the system 100.

The system 100, as illustrated, includes a pump 103 for moving blood from the patient 101 to the mixing chamber 104. In some implementations, the pump operates continuously, while in other implementations the pump works intermittently, and only activates when the level of whole blood in the mixing chamber 104 or manifold falls below a set threshold. In some implementations, the flow rate of the pump is configurable, such that the rate the blood exits the patient can be configured to be faster or slower than if no pump was used. In yet other implementations, no external pump is required. In this example, the blood is transported to the mixing chamber 104 by the pressure generated by the patient's own heart. In some implementations, flow or pressure is monitored in the network, and these measurements in turn control the pump. Example pumps can include, but are not limited, to peristaltic pumps, impeller pumps or any other pump suitable for flowing blood.

As illustrated in the system 100, capture particles are also pumped into the mixing chamber 104. In some implementations, the capture particles are polystyrene beads or liposomes encapsulating an acoustically active fluid. The capture particles are described in greater detail below. A pump 106 pumps the capture particles from a reservoir 115 to the mixing chamber 104. In the mixing chamber 104, affinity particles embedded within the surface of the capture particles bind to undesired particles, cells, or toxins to be removed from the blood.

As illustrated in FIG. 1, the capture particles are injected into the mixing chamber 104. In other implementations, the capture particles are injected into the manifold system 107 or directly into the separation channels of the microfluidic flow chamber 108. In some implementations, the system 100 does not use capture particles. For example, the components (e.g., red blood cells) of the fluid to be cleansed may be intrinsically acoustically active. For example, cells or other objects may have an acoustic contrast factor sufficiently different than that of the blood or other fluid and are therefore "acoustically active." These cells or other objects can be directed with the acoustic transducer 109.

As illustrated in system 100, the blood containing undesirable particles and the capture particles enter the mixing chamber 104. In some implantations, the contents of the mixing chamber are continuously agitated to improve distribution of the capture particles throughout the blood and undesirable particles such that the capture particles bind to the undesirable particles. In some implementations, anticoagulants or blood thinners are introduced into the mixing chamber 104 to assist the blood as it flows through the system 100. In some implementations, the mixing chamber 104 contains a heating element for warming the contents of the mixing chamber 104.

The contents of the mixing chamber 104 then flow into the manifold system 107, as illustrated by system 100. The manifold system 107 is described further in relation to FIGS. 3-12, among others. As an overview, the manifold system 107 flows the blood, undesirable particles, and capture particles into the inlets of the plurality of separation channels of the microfluidic flow chamber 108. In some implementations, multiple microfluidic flow chambers described herein are stacked to process relatively large volumes of blood or other fluids. The manifold system 107 distributes the blood to each of the separation channels of the stacked microfluidic flow chambers. In some implementations, the manifold system 107 is configured to distribute shear sensitive fluids, such as blood, to each of the separation channels without damaging the shear sensitive fluids. In some implementations, the manifold system 107 is also configured to receive the shear sensitive fluid from the microfluidic flow chamber 108 after the fluid has flowed through the microfluidic flow chamber 108.

The manifold can include biomimetic features. For example, the manifold can include gradual curving channels rather than right angles. In some implementations, the biomimetic features can include channels within the manifold that mimic vascular channels. For example, the channels split at bifurcations. After a bifurcation the size of the channel is reduced according to Murray's Law. In some implementations, the manifold includes trunk and branch channels, where supply channels flowing to each of the microfluidic flow chambers branch from a main supply trunk. Additional information regarding the biomimetic manifold system 107 can be found in U.S. patent application Ser. No. 13/736,685, titled Compact Hydraulic Manifold Structure for Shear Sensitive Fluids, which is incorporated herein by reference in its entirety. The system 100 can also include a collection manifold that condenses the plurality of separation channels of the stacked microfluidic flow chambers into the first outlet 111 and the second outlet 112, which can also be referred to as collection channels. In some implementations, the system 100 can include multiple collection and input manifolds that can each collect or supply fluid to a portion of the separation channels.

In the system 100, the microfluidic flow chamber 108 contains a plurality of separation channels. The microfluidic flow chamber 108 and separation channels are described further in relation to FIGS. 3-20, among others. The capture particles and undesirable particles are driven with standing acoustic waves to outlets. In other implementations, the acoustic wave is activated intermittently. In some implementations, the separation occurs during a single stage, while in other implementations, the separation occurs over a plurality of stages. In some implementations, the microfluidic flow chamber is disposable.

As shown in the illustrations of system 100, the microfluidic flow chamber 108 sits atop an acoustic transducer 109. In some implementations, the system 100 contains a single acoustic transducer 109, while in other implementations the system 100 contains a plurality of acoustic transducers 109.

In some implementations, the acoustic transducer 109 is glued to the microfluidic flow chamber 108. In other implementations the microfluidic flow chamber 108 is clamped to the acoustic transducer 109 so the microfluidic flow chamber may easily be removed from the system. In other implementations the adhesive material connecting the acoustic transducer 109 to the microfluidic flow chamber 108 is removable, for example by heating the adhesive.

The acoustic transducer 109 imposes a standing acoustic wave on the separation channels of the microfluidic flow chamber 108 transverse to the flow of the fluid within the microfluidic flow chamber 108. The standing acoustic waves are used to drive fluid constituents towards or away from the walls of the separation channels or other aggregation axes.

More particularly, the dimensions of the separation channels are selected based on the wavelength of the imposed standing wave such that pressure nodes are generated in each of the separation channels. The capture particles are driven to different positions within the separation channels based on the sign of their acoustic contrast factor at a rate which is proportional to the magnitude of their contrast factor. Capture particles or other elements with a positive contrast factor (e.g. the formed elements of blood) are driven towards the pressure nodes within the interior of the separation channel. In contrast, elements with a negative contrast factor are driven toward the pressure antinodes.

Based on these principles, formed elements of blood can be separated from capture particles (and thus the undesirable particles bound to the capture particles). For example, capture particles can be selected to have negative contrast factors, which is opposite to the positive contrast factors of the formed elements of blood. Thus, in response to the standing acoustic wave, the formed elements are driven towards the resulting pressure node while the capture particles are driven towards the antinodes.

In other examples, one type of blood cell can be separated from another because of the differing size, density, or compressibility of the cell types. For example lymphocytes may be separated from other white blood cells, red blood cells, and platelets. In some examples, analytes, diseased cells, or pathogenic cells, including bacteria, can be separated from normal blood cells.

As illustrated in the system 100, the cleansed blood exits the microfluidic flow chamber 108 at a first outlet 110. From there the blood is returned to the patient 101 via an intravenous supply line 111. In some implementations, the blood in the supply line 111 is reheated to body temperature before returning to the patient 101. In other implementations an infusion pump is used to return the blood to the patient 101, while in the system 100 the pressure generated in the system by pumps 103 and 106 is adequate to force the blood to return to the patient 101.

As illustrated in the system 100, waste material (e.g. the capture particle and undesirable particles) exit the microfluidic flow chamber 108 and enter a waste collection unit 113. In some implementations, the waste collection unit 113 contains a capture particle recycler. The capture particle recycler unbinds the undesirable particles from the capture particles. The capture particles are then returned to the reservoir 115 via tubing 114. The undesirable particles are then disposed of. In some implementations, the undesirable particles are saved for further testing.

In some implementations, the microfluidic flow chamber 108 can be used for other methods than blood cleansing such as, but not limited to, apheresis and analytical sample preparation. For example, in an apheresis process cells, blood plasma, or other waste is removed from the blood and discarded. A replacement fluid or suspension can be added back to the blood to replace the volume lost from the removal of the waste. In an example where the microfluidic flow chamber 108 is used for sample preparation, the microfluidic flow chamber 108 can be used to flow extract a desired fraction of cells or particles from a sample or to remove particles or cells to leave purified liquid fraction.

While the system 100 is described above for the in-line cleansing of a patient's blood, in alternative implementations, the system 100 can be used to cleanse stored blood or other stored fluids. For example, the system 100 can be used to cleanse collected blood for later infusion to help ensure the safety of the blood or it can be used to prepare blood for analysis.

Figure 2:
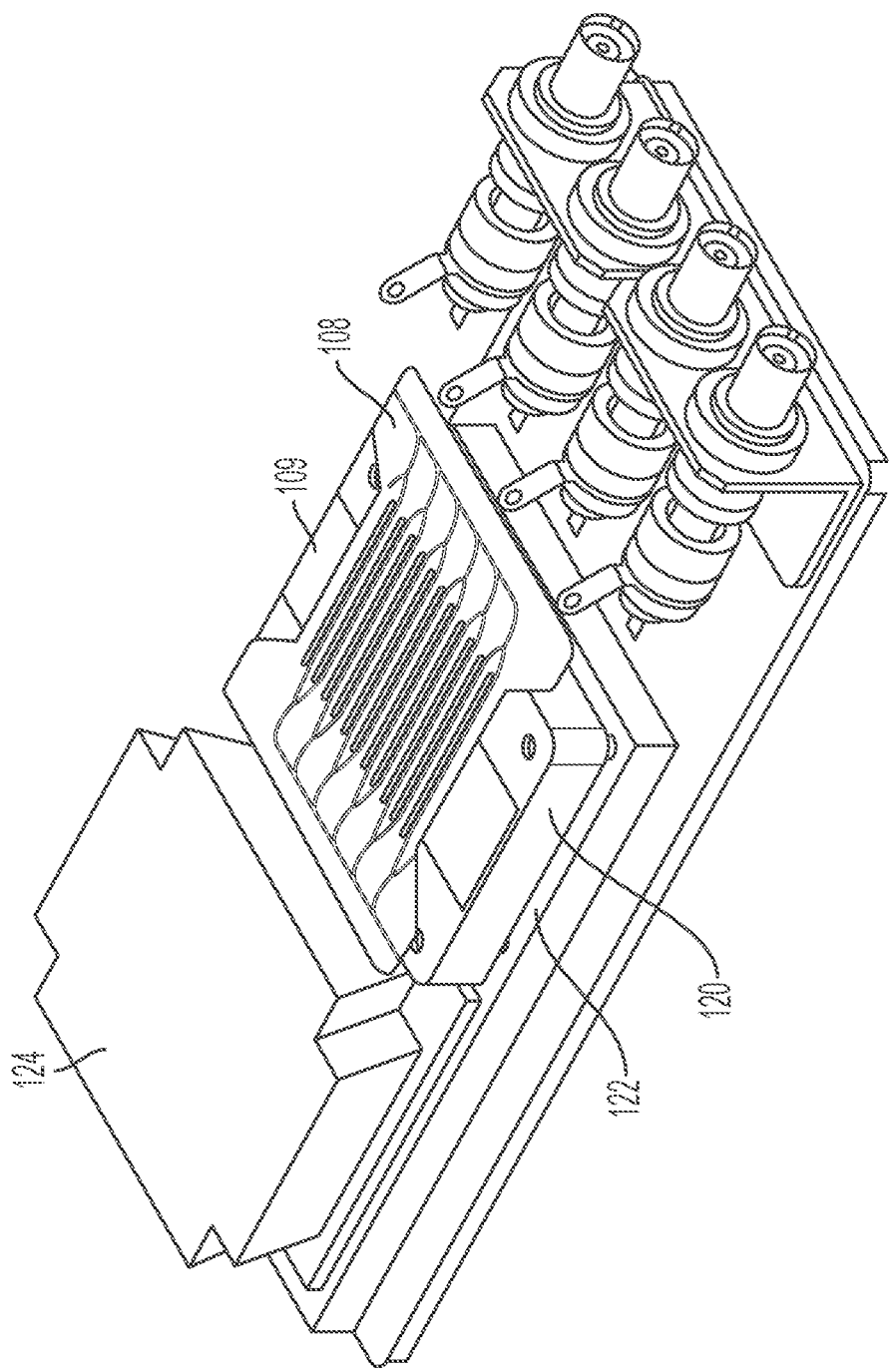
FIG. 2 illustrates an example implementation of the system for separating contents of a fluid.

FIG. 2 illustrates one example implementation of the system for separating contents of a fluid. The system includes the microfluidic flow chamber 108. The microfluidic flow chamber 108 can be positioned against the acoustic transducer 109. The temperature of the acoustic transducer 109 is controlled via a heat sink 120 and a peltier device 122. The heat sink 120 and the peltier device 122 can prevent the acoustic transducer 109 from overheating the blood flowing through the microfluidic flow chamber 108 and maintain the temperature of the blood in or near physiological temperature ranges. The system can also include a heat exchanger 124. The heat exchanger 124 aid in dissipation of heat generated by the transducer. The acoustic transducer 109, heat sink 120, and peltier device 122 can be components of a base substrate.

Figure 3:
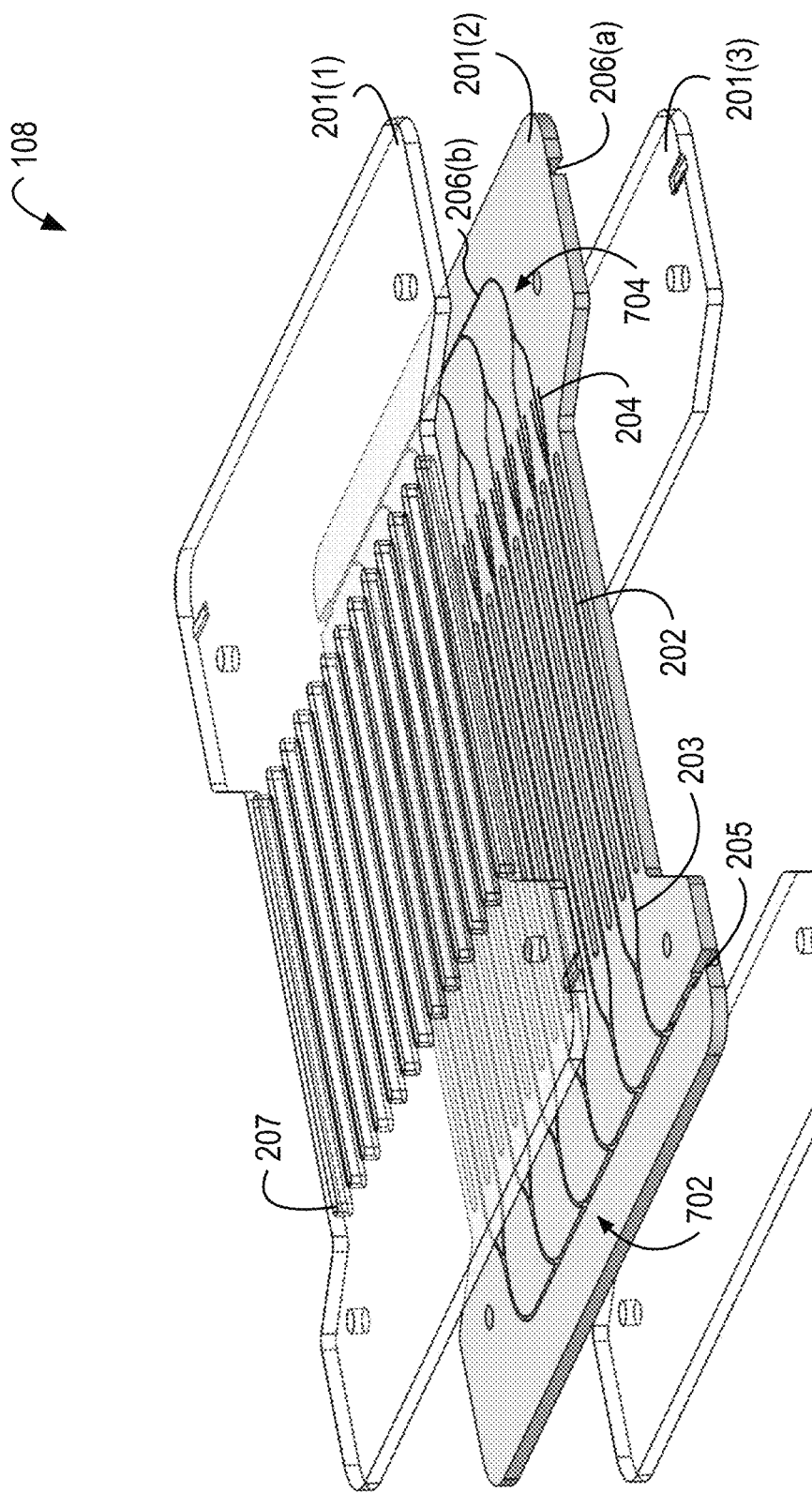
FIG. 3 illustrates an example microfluidic flow chamber that can be used in the system illustrated in FIG. 1.

FIG. 3 illustrates an example microfluidic flow chamber 108 that can be used in the example implementation of the system illustrated in FIGS. 1 and 2. The microfluidic flow chamber 108 includes a first substrate 201(1), a second substrate 201(2), and a third substrate 201(3), which can be generally referred to as substrates 201. The substrate 201(2) includes a plurality of separation channels 202. The substrate 201(2) also includes the distribution manifold 702 and the collection manifold 704, which can be implementations of the manifold system 107 illustrated in FIG. 1. The distribution manifold 702 can include a feed channel 205 that can serve as a trunk to the distribution manifold 702. The feed channel 205 can branch into a plurality of inlets 203 that form the start of the separation channels 202. The separation channels 202 can branch to form a plurality of outlets 204. For example, the separation channels 202 can branch to form a central and two lateral outlets. The outlets 204 can be a component of the collection manifold 704. The distribution manifold 702 can be defined in a first face of the substrate 201(1). The collection manifold 704 can be defined in the first face and a second face of the substrate 201(1). Each portion of the collection manifold 704 that is defined in a different face of the substrate 201(1) can form a collection manifold for one or more of the channels outlets 204. For example, each channel 202 can include one or more outlets 204 that collect the focused particles, which can exit to a collection manifold on first face of the substrate 201(1) and each channel 202 can include one or more outlets 204 that collect the fluid substantially free of the focused particles, which can exit to a collection manifold on the second face of the substrate 201(1). The distribution manifold 702 can include portions defined in the first face and the second face of the substrate 201(2). For example, the portion of the distribution manifold 702 defined on one face can feed the separation channels 202 with the fluid from which the particles are to be removed. The portion of the distribution manifold 702 defined on another face of the substrate 201(2) can feed a buffer fluid into separation channels 202. For example, the separation channels 202 can include three inlets. The central inlet can supply a buffer fluid to the separation channel 202. The lateral inlets can supply the blood (or other fluid from which the particles are to be remove) toward the lateral walls of the separation channels 202. The acoustic wave can drive the blood cells (or other acoustically active particles) into the buffer flowing through the central portion of the separation channel 202.

The microfluidic flow chamber 108 can include three substrates 201. In some implementations, the microfluidic flow chamber 108 can include more than three substrates 201 or can include fewer than three substrates 201. For example, the microfluidic flow chamber 108 can include a stacked configuration that includes a plurality of substrates 201 that include channels 202. The channels 202 of the microfluidic flow chamber 108 can be machined into the faces of the substrate 201(2). The channels 202 can be created in the face of the substrates 201 using, for example, direct lithography, photopatternable resists, injection molding, direct micromachining, deep reactive ion etching (ME), hot embossing, or any combinations thereof. When the substrates 201 are coupled together, the top substrate 201(1) can form a wall (e.g., a ceiling) of the channels 202 machined into the top face of the substrate 201(2) and the bottom substrate 201(3) can form a wall (e.g., a floor) of the channels 202 machined into the bottom of the substrate 201(2). The substrates 201 can be coupled together with, for example, thermocompression bonding, mechanical coupling (e.g., clamps), adhesives, or epoxies.

In some implementations, the channels 202 can also be machined into the top substrate 201(1) and the bottom substrate 201(3). In some implementations, the bottom substrate 201(3) can divided into multiple parts or can be cut away in the region of the separation channels 202 in order to avoid interfering with the acoustic properties of the separation channels or to avoid interfering with the coupling of the transducer to the substrates. In some implementations the transducer is coupled to a face of the substrate 201(1) and in others it is coupled to a face of the substrate 201(2). The channels 202 machined into the top face of the substrate 201(1) can be fluidically coupled with the channels 202 machined into the bottom face of the substrate 201(1) through via channels. The via channels can also be referred to as translation channels, connecting channels, microfluidic channels, or channels.

As illustrated, the distribution manifold 702 is machined into the top face of the substrate 201(2). The distribution manifold 702 can include the feed channel 205 that branches into the inlets 203 and the separation channels 202. The separation channels 202 can then branch into the central and lateral outlets 204. The central outlet 204 can be machined into the top face of the substrate 201(2) and can feed into the collection channel 206(b) of the collection manifold 704. The lateral outlets 204 can be coupled with the collection channel 206(a) of the collection manifold 704. The lateral outlets 204 can be pass through the via channels to channels machined in the bottom face of the substrate 201(2), which can then feed the collection channels 206(a).

Figure 4:
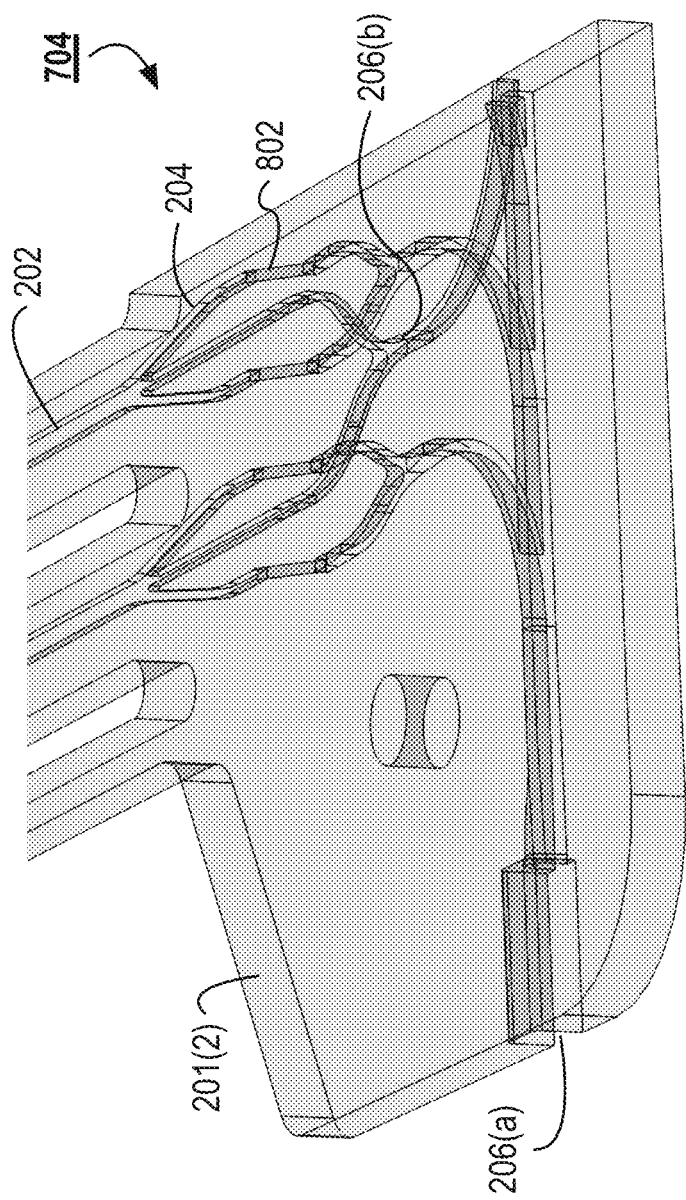
FIG. 4 illustrates a wire frame detail of the collection manifold from the collection manifold illustrated in FIG. 3.
Figure 5:
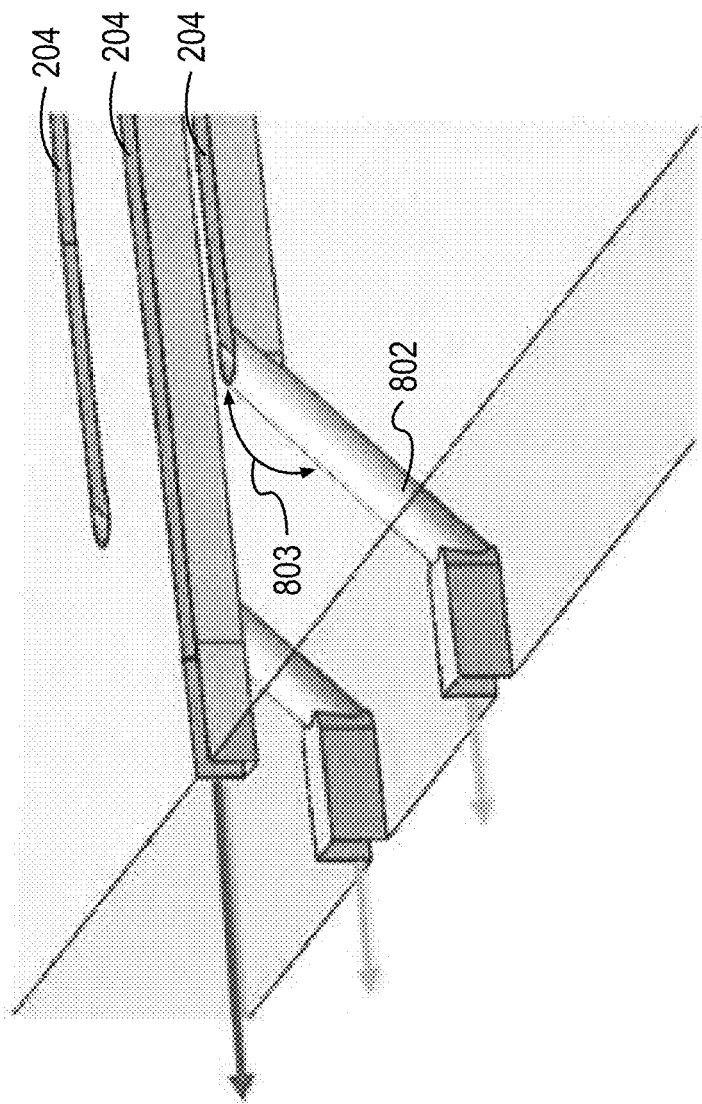
FIG. 5 illustrates a section view of the wire frame model illustrated in FIG. 4.

FIG. 4 illustrates a wire frame model of a detail of the collection manifold 704 from the collection manifold 704 illustrated in FIG. 3. FIG. 5 illustrates a different view of the wire frame model illustrated in FIG. 4. The separation channels 202 branch into the central and lateral outlets 204. The neighboring central outlets 204 can merge and flow into the first collection channel 206(b) that is machined into the top face of the substrate 201(2). In some implementations, more than two central outlets 204 can merge and flow into a first collection channel 206(b). For example, between about 2 and about 10, between about 2 and 6, or between about 2 and 4 central outlets 204 can merge into a first collection channel 206(b). The collection manifold 704 can include a plurality of collection layers. For example, 20 central outlets 204 can merge into 10 different collection channels of a first collection layer, which can merge into 5 different collection channels of a second collection layer. The collection channels can continue to merge until a single collection channel remains as an output. A plurality of collection channels 206(b) can branch serially off of an outlet trunk as illustrated in FIG. 3.

The lateral outlets 204 can pass to a collection channel 206(a) formed in the bottom face of the substrate 201(2) by via channels 802. The via channels 802 can fluidically couple channels machined into a first face of a substrate 201 to channels machined into a second face of the substrate 201. For example, the via channels 802 can coupled the lateral outlets 204 formed in the top face of the substrate 201(2) with the collection channel 206(a) formed in the bottom face of the substrate 201(2). The via channels 802 can enable fluid routing in the microfluidic flow chamber 108. The via channels 802 can enable fluid routing in a substrate 201 such that collection channel 206(b) and 206(a) can cross each other without intersecting.

For example, as illustrated in FIG. 4, the middle outlet 204 can continue to flow on a first face of the substrate 201(2) and into a collection channel 206(b) that is machined into the first face of the substrate 201(2). The lateral outlets 204 can each flow into a via channel 802 and into a collection channel 206(a) that is machined into a second face of the substrate 201(2).

The via channels 802 can be manufactured by drilling through the substrate 201 at a predetermined angle 803. The via channels 802 can be laser or mechanically drilled through the substrates 201. The predetermined angle 803 can be between about 10° and about 80°, between about 15° and about 75°, between about 20° and about 70°, between about 25° and about 65°, between about 30° and about 60°, between about 35° and about 55°, or between about 40° and about 50°. In some cases, the predetermined angle 803 is about 45°. The predetermined angle 803 can be less than 45°. The predetermined angle 803 can be selected based on the fluid flowing through the channels. For example, some fluids (e.g., blood) may be more sensitive to shear forces or other forms of trauma. For these fluids a smaller angle can be selected when compared to fluids that are less sensitive to trauma. The predetermined angle 803 can be selected to reduce trauma to the blood (or other fluid) flowing through the via channels 802 and channels 202. The predetermined angle 803 can be selected to prevent clotting of the blood (or other fluid) at the transition into and out of the via channels 802.

Figure 6:
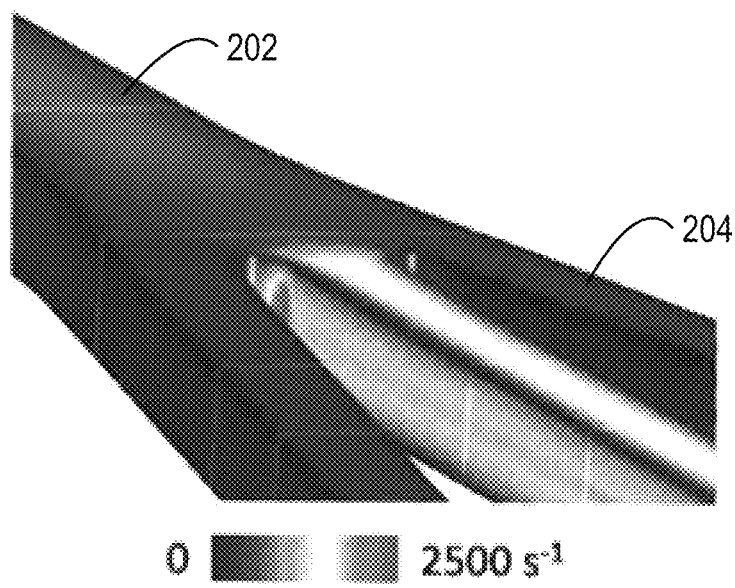
FIGS. 6-8 illustrate the modeled wall shear rates experienced within the microfluidic flow chamber illustrated in FIG. 3.
Figures 7, 8:
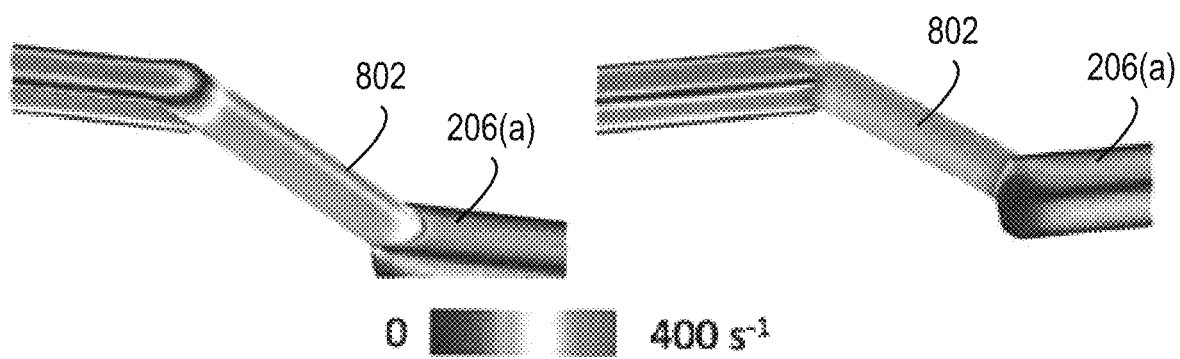

FIGS. 6-8 illustrate the modeled wall shear rates experienced within the microfluidic flow chamber 108. FIG. 6 illustrates the trifurcation from the channel 202 to the central and lateral outlets 204. As illustrated, the lateral outlets 204 experience a low wall shear rate while the central outlet 204 experiences a relatively higher wall shear rate. FIGS. 7 and 8 illustrate the modeled wall shear rates experienced near the via channels 802. As illustrated, the via channels 802 experience relatively greater wall shear rates than the collection channel 206(a). In all cases however, the shear rates are acceptable because they are below the threshold that would be expected to damage blood cells. The effective diameters of the central and lateral outlets and the diameters of the via channels 802 can be adjusted to improve uniformity of shear throughout the manifolds. To enable bubbles to pass through the microfluidic chamber 108, the diameters of the via channels 802 can be larger than the width of the of lateral outlets 204 and smaller than the width of the collection channels 206 with which they intersect.

FIGS. 9 and 10 illustrate the wall shear rates and fluid velocity, respectively, experienced in the transition between the via channels 802 and the collection channel 206(a). FIGS. 9 and 10 illustrate the shear and velocity is low in the "backstep" portion of the transition. The transition can be configured to reduce trauma to the blood flowing though the transition; however, the transition is configured such that the shear and velocity are not too low in the backstep (and other portions of the microfluidic flow chamber) as to generate areas of stagnation where clots can form or areas of recirculating flow. In other designs, the via channels 802 and the channels can be manufactured such that a "backstep" is not formed.

Figure 12:
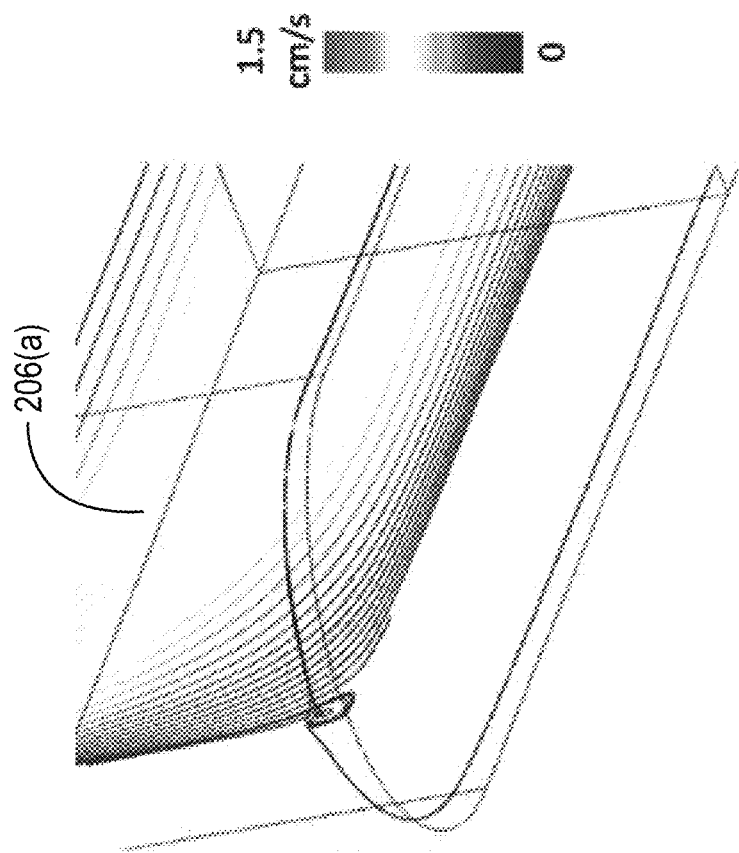
FIGS. 11 and 12 illustrate plots of streamlines through the transition from the via channels to the collection channels.
Figure 11:
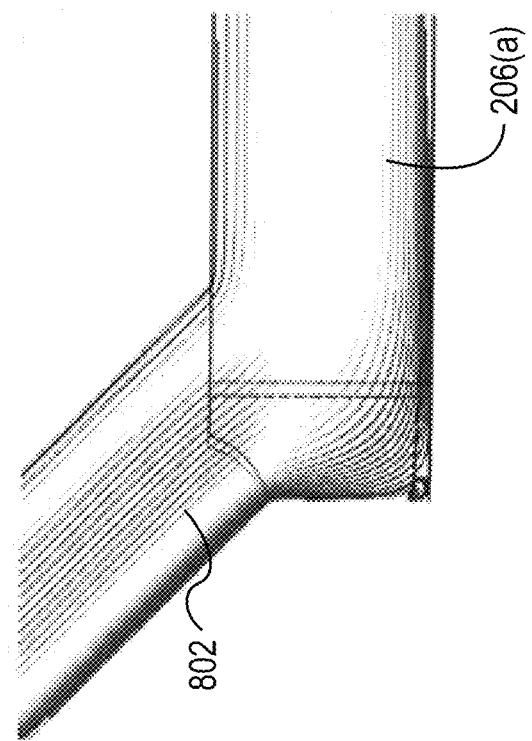

FIGS. 11 and 12 illustrate plots of streamlines through the transition from the via channels 802 to the collection channels 206(a). As illustrated, the transition is configured to not include recirculating or stagnate flow that can cause clotting or other issues with flow through the microfluidic flow chamber 108.

Figure 13:
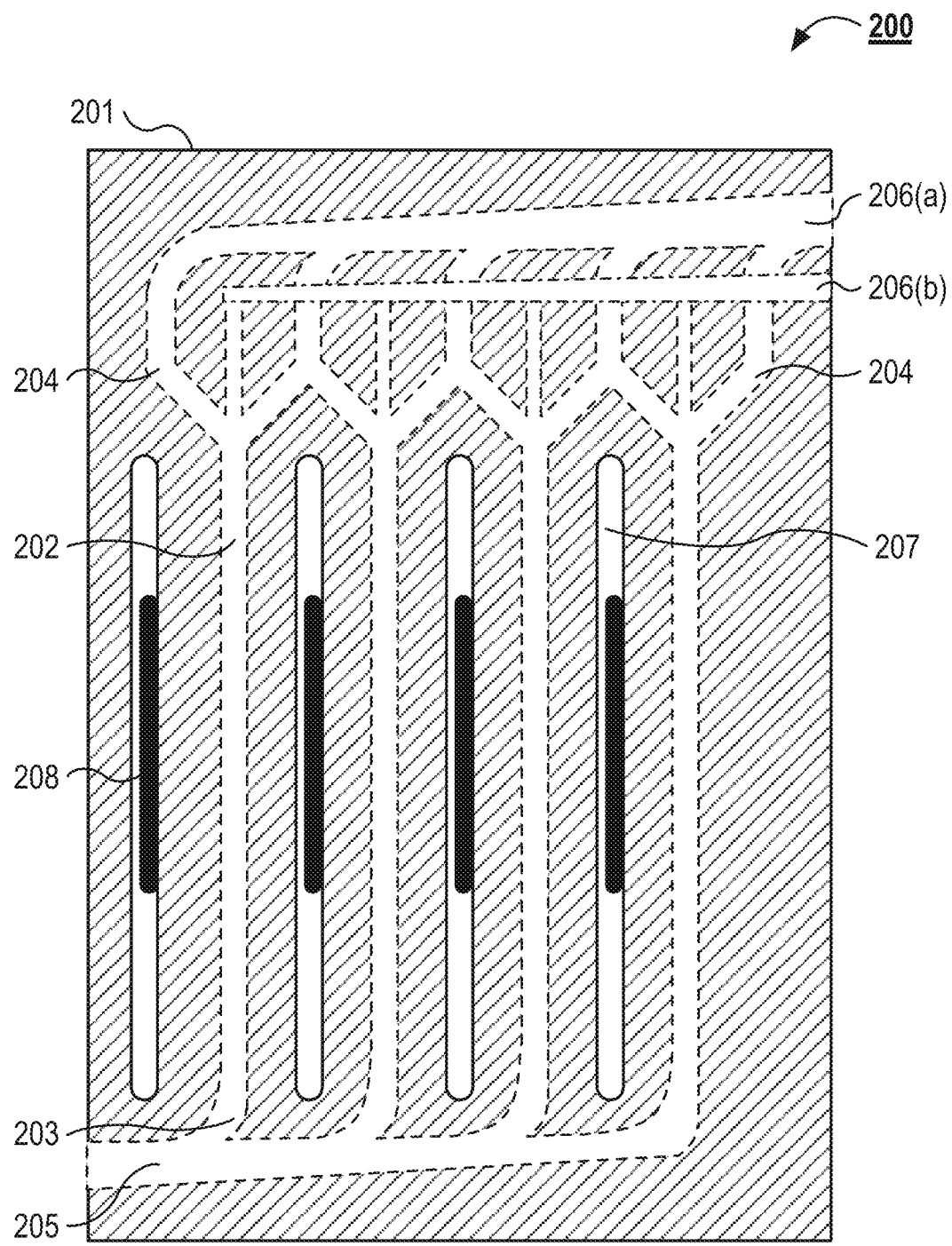
FIG. 13 illustrates a top view schematic of an example microfluidic flow chamber as can be used in the system illustrated in FIG. 1.

FIG. 13 illustrate a top view schematic of an example microfluidic flow chamber 108 as can be used in the system 100 illustrated in FIGS. 1 and 2. Also referring to FIG. 3, the microfluidic flow chamber 108 includes a substrate 201. The substrate 201 defines a plurality of separation channels 202. Each of the separation channels 202 includes an inlet 203 and multiple outlets 204. Each inlet 203 is coupled to a feed channel 205, and each of the outlets 204 are coupled to a collection channel 206. As illustrated, the microfluidic flow chamber 108 includes a first collection channel 206(a) and a second collection channel 206(b). The substrate 201 also defines a plurality of isolation slots 207. The acoustic transducers 208 protrude from a base substrate below the substrate 201 and project through isolation slots 207. The substrate 201 can be configured to couple with the base substrate. For example, and also referring to FIG. 3, the substrate 201(3) can include a plurality of alignment markers that are configured to receive posts or protrusions from the base substrate.

The substrate 201 defines the separation channels 202 and the isolation slots 207. In some implementations, the substrate 201 includes rigid materials such as silicon, glass, metals, or other materials that establish a high acoustic contrast between the fluid flowing though the separation channels 202 and the substrate 201. In other implementations, the substrate 201 includes relatively more elastic materials, which establish a lower acoustic contrast between the fluid flowing the separation channels 202 and the substrate 201. These materials can include thermoplastics, such as, polystyrene, acrylic (polymethylmethacrylate), polysulfone, polycarbonate, polyethylene, polypropylene, cyclic olefin copolymer, silicone, liquid crystal polymer, and polyvinylidene fluoride.

The substrate 201 of the microfluidic flow chamber 108 includes multiple separation channels 202. The separation channels 202 are formed into an array of separation channels 202. The array of separation channels 202 can include between about 2 and about 100, between about 2 and about 50, between about 10 and about 40, or between about 20 and about 30 separation channels. The inlet 203 of each of the separation channels 202 is coupled to the feed channel 205 that provides fluid to each of the separation channels 202. The feed channel 205 and the separation channels 202 can be configured in a trunk and branch configuration. For example, as illustrated in FIG. 13, the feed channel 205 can narrow as separation channels 202 branch off the feed channel 205. The trunk and branch configuration can also include smooth and gradual transitions between the feed channel 205 and each of the separation channels 202. The transitions between the feed channel 205 and the separation channels 202 are configured to reduce or prevent damage to blood flowing through the microfluidic flow chamber 108 and to prevent clotting. The feed channel 205 receives fluid from the manifold system described herein. The separation channels 202 are configured to branch into multiple outlets 204 toward their downstream end. As illustrated, the separation channels 202 include a central outlet and two lateral outlets (generally referred to as outlets 204). The two lateral outlets of each separation channel 202 are coupled to the collection channel 206(a), and the central outlet of each separation channel 202 is couple to the collection channel 206(b). As with between the feed channel 205 and the separation channels 202, the transitions between the separation channels 202 and the collection channels 206(a) and 206(b) are smooth and gradual.

In some implementations, the capture particles are aligned toward an aggregation axis that is along a central axis of each of the separation channels. In these implementations, the fluid flowing into the central outlet 204 is enriched with the capture particles, and the fluid flowing into the lateral outlets 204 is depleted of the capture particles. In other implementations, the capture particles are aligned toward the walls of each of the separation channels 202 by the acoustic transducers 208. In these implementations, the fluid flowing into the lateral outlets 204 is enriched with the capture particles and the fluid flowing into the central outlet 204 is depleted of the capture particles.

In some implementations, the undesirable cells are aligned toward an aggregation axis that is along a central axis of each of the separation channels. In these implementations, the fluid flowing into the central outlet 204 is enriched with undesirable cell types, and the fluid flowing into the lateral outlets 204 is enriched with the desired cell type. In other implementations, the undesirable cells are aligned toward the walls of each of the separation channels 202 by the acoustic transducers 208. In these implementations, the fluid flowing into the lateral outlets 204 is enriched with the undesirable cells and the fluid flowing into the central outlet 204 is enriched with the desired cell type.

As illustrated in FIG. 13, the collection channel 206(b) is in a different plane than the separation channels 202 and the collection channel 206(a). The collection channel 206(b) is coupled to each of the central outlets 204 by a fluidic via between the plane of the separation channels 202 and the collection channel 206(b). In some implementations, the collection channel 206(b) is in the same plane as the central outlets 204 and the collection channel 206(a) is in a different plane than the lateral outlets 204 and separation channels 202.

The microfluidic flow chamber 108 illustrated in FIG. 13 also includes a plurality of isolation slots 207. The isolation slots 207 are channels that run parallel to the separation channels 202. The isolation slots 207 have a height equal to the thickness of the substrate 201 and form air gaps through the substrate 201 between adjacent separation channels 202. For example, the isolation slots 207 can be milled or cut through the substrate 201. The air gaps between the adjacent separation channels 202, as provided by the isolation slots 207, isolate the acoustic effects of waves from the acoustic transducers 208 to specific separation channels 202.

In some implementations, the isolation slots 207 run substantially the entire length of the separation channels 202, and in other implementations, the isolation slots 207 run along a length of the separation channels 202 only near the acoustic transducers 208. Each of the substrates 201 can include isolation slots 207 or a subset of the substrates 201 can include the isolation slots 207. For example, the substrate 201(1) and the substrate 201(2) can include the isolation slots 207. The isolation slots 207 are between about 100 µm and about 5 mm, between about 200 µm and about 3 mm, between about 300 µm and about 2 mm, or between about 500 mm and about 1 mm wide. The separation channels 202 are between about 1 cm and about 10 cm, about 2 cm and about 8 cm, or about 3 cm and about 5 cm long.

A plurality of acoustic transducers 208 coupled to the microfluidic flow chamber 108. The acoustic transducers 208 can couple with a portion of the substrate 201(2) exposed by a gap in the substrate 201(3) or the acoustic transducers 208 can be coupled to the substrate 201(3). The acoustic transducers 208 are, for example, piezoelectric transducers as described above in relation to FIG. 1. Each of the acoustic transducers 208 are configured to imposes a standing acoustic wave on one of the separation channels 202 of the microfluidic flow chamber 108. The standing acoustic wave is applied transverse to the flow of the fluid through the separation channels 202. The standing acoustic waves generate pressure nodes and pressure antinodes within the separation channels 202 that drive the capture particles towards or away from the walls of the separation channels 202 or toward other aggregation axes. The acoustic wave may be applied continuously or intermittently.

Figure 14:
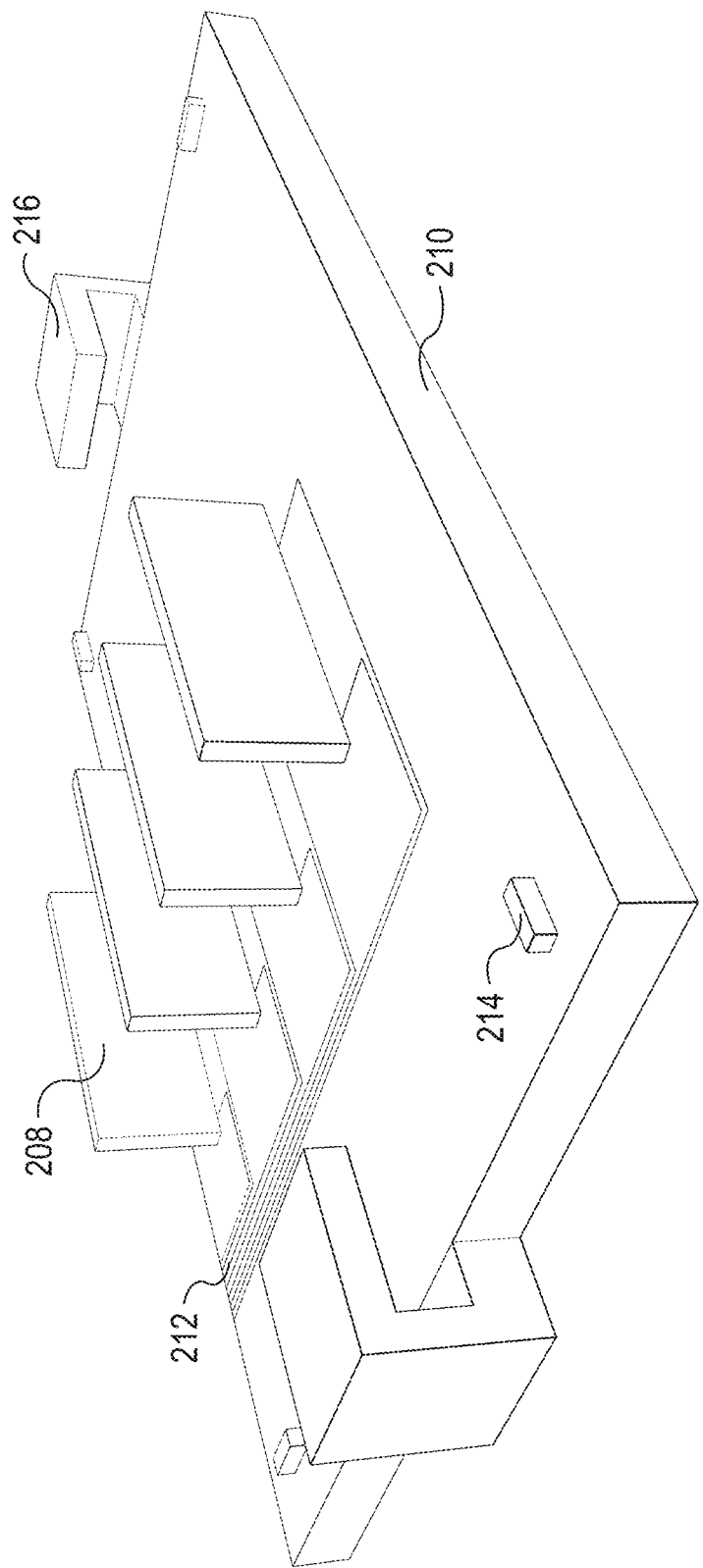
FIG. 14 illustrates an isometric view of an example base substrate to which the microfluidic flow chamber illustrated in FIG. 13 is to be coupled.

FIG. 14 illustrates an isometric view of an example base substrate 210 to which the microfluidic flow chamber 108, illustrated in FIG. 13, can be coupled. The base substrate 210 includes the acoustic transducers 208, which are powered via electrical traces 212. The base substrate 210 includes a plurality of orientation markers 214. The base substrate 210 also include clamps 216 to clamp a microfluidic flow chamber to the base substrate 210. In some implementations, the microfluidic flow chamber 108 can be coupled with the acoustic transducers 208 and the clamps clamp the acoustic transducers 208 to the base substrate 210.

The acoustic transducers 208 are mounted to the base substrate 210. The acoustic transducers 208 project perpendicular to the base substrate 210. As illustrated in FIG. 13, when the microfluidic flow chamber 108 is coupled to the base substrate 210 each of the acoustic transducers 208 project into one of the isolation slots 207. The acoustic transducers 208 are coupled to one the walls of the of the isolation slots 207, which is a shared wall with one of the adjacent separation channels 202. For example, the acoustic transducers 208 can be coupled to the inner walls of the isolation slots 208 by glycerol, glue, film, gel, or other material configured to efficiently transfer waves from the acoustic transducers 208 to the inner wall of the isolation slots 207.

The base substrate 210 includes a plurality of electrical traces 212. The electrical traces 212 provide power to and ground each of the acoustic transducers 208. In some implementations, the electrical traces 212 terminate in a multi-pin electrical connector that enable each of the acoustic transducers 208 to be controlled independently of one another.

The base substrate 210 also includes a plurality of orientation markers 214. The orientation markers 214 are raised pins positioned towards each of the corners of the base substrate 210. The bottom of the substrate 201 illustrated in FIG. 13 includes recesses that mate with each of the orientation markers 214. The orientation markers 214 can ensure the substrate 201 is properly aligned with the base substrate 201—therefore ensuring the acoustic transducers 208 are properly aligned with the separation channels 202.

The base substrate 210 also includes clamps 216. As illustrated, the clamps 216 are illustrated in their closed (or clamped) position. Once the substrate 201 is placed on the base substrate 210 and properly orientated using the orientation markers 214, the clamps 216 are closed to reversibly couple the substrate 201 to the base substrate 210. In some implementations, the base substrate 210 includes a clamp 216 on each of its four sides rather than just two sides as illustrated in FIG. 14.

Figure 15:
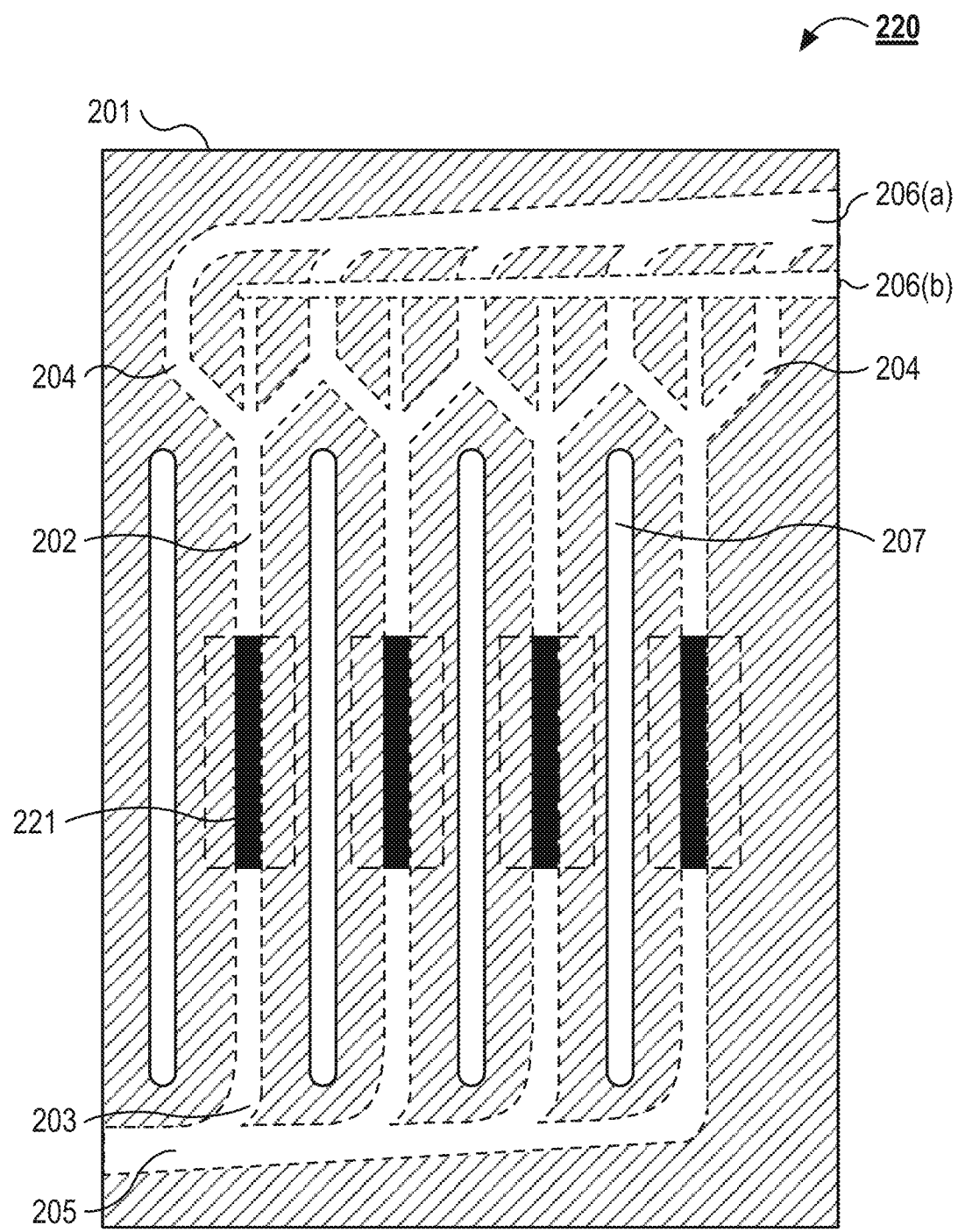
FIG. 15 illustrate a top view schematic of another example microfluidic flow chamber as can be used in the system illustrated in FIG. 1.

FIG. 15 illustrates a top view of an example microfluidic flow chamber 108. As described above in relation to FIG. 13, the microfluidic flow chamber 108 includes a substrate 201. The substrate 201 defines a plurality of separation channels 202. Each of the separation channels 202 includes an inlet 203 and multiple outlets 204. Each inlet 203 is coupled to a feed channel 205, and each of the outlets 204 are coupled to a collection channel 206. As illustrated, the microfluidic flow chamber 108 includes a first collection channel 206(a) and a second collection channel 206(b). The substrate 201 also defines a plurality of isolation slots 207. The microfluidic flow chamber 108 can couple with or include acoustic transducers 221. As described below in relation to FIG. 16, the acoustic transducers 221 lie flat on a base substrate (not shown) below the substrate 201. The acoustic transducer 221 are coupled to a bottom wall of each of the separation channels 202.

Figure 16:
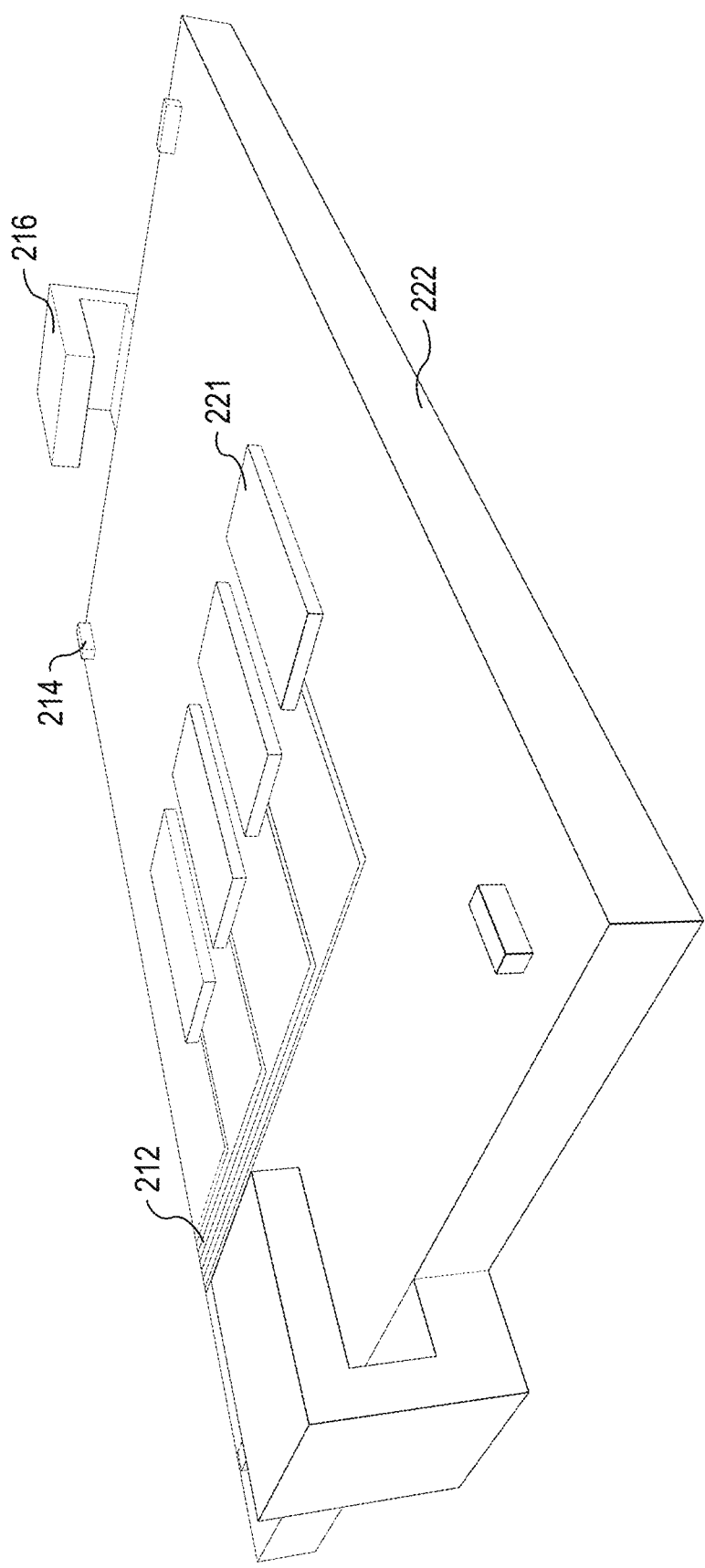
FIG. 16 illustrates an isometric view of an example base substrate to which the microfluidic flow chamber illustrated in FIG. 15 is to be coupled.

FIG. 16 illustrates an isometric view of an example base substrate 222 to which the microfluidic flow chamber 108, illustrated in FIG. 15, is coupled. The base substrate 222 includes the acoustic transducers 221, which are powered via the electrical traces 212. The base substrate 222 includes a plurality of orientation markers 214. The base substrate 222 also include claims 216 to clamp a microfluidic flow chamber to the base substrate 210. The clamps 216, orientation markers 214, and electrical traces 212 can be similar to those described above. The acoustic transducers 221 lie flat on the base substrate 222 and are configured to project an acoustic wave upward into the separation channels 202 of the microfluidic flow chamber 108. In some implementations, the microfluidic flow chamber 108 includes recesses to receive the acoustic transducers 221, enabling the acoustic transducers 221 to provide an orientation function similar to the orientation markers 214. In some implementations, a single, larger acoustic transducer 221 is coupled to the base substrate 222 rather than a plurality of smaller acoustic transducers 221.

Figure 17:
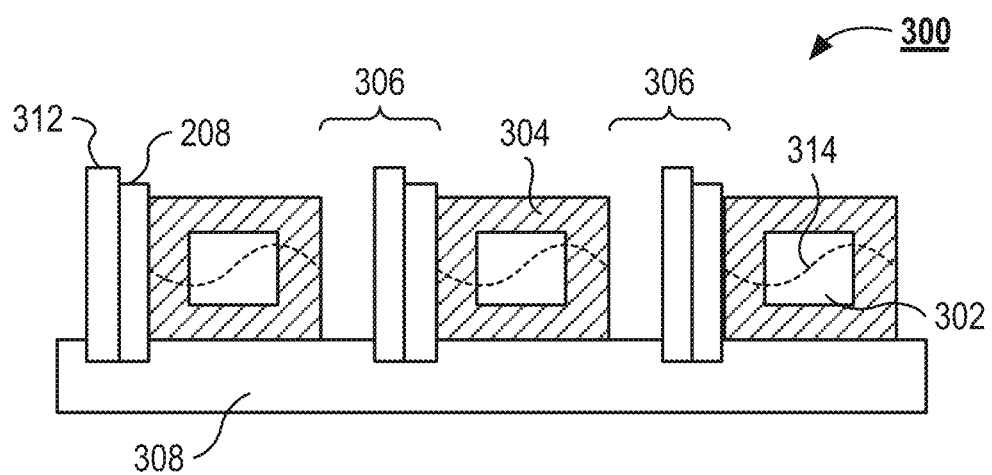
FIG. 17 illustrate a cross-sectional view of an example microfluidic flow chamber as can be used in the system illustrated in FIG. 1.

FIG. 17 illustrates a cross-sectional view of an example microfluidic flow chamber 300. The microfluidic flow chamber 300 includes three separation channels 302 that are defined within a plastic substrate 304. Each adjacent separation channel 302 is separated by an isolation slot 306. The substrate 304 that defines the separation channels 302 and the isolation slots 306 sits atop a base substrate 308. An acoustic transducer 208 is coupled to an inner wall of each of the isolation slots 306. A heat sink 312 is coupled to each of the acoustic transducers 208.

The substrate that defines the separation channels 302 can have a thickness between about 0.3 mm and about 3 mm, between about 0.5 mm and about 2 mm, or between about 0.5 mm and about 1.5 mm. The width of the separation channel can be between about 0.2 mm and about 1.5 mm, between about 0.25 mm and about 1 mm, or between about 0.25 mm and about 0.75 mm. The depth (or height) of the separation channels 302 can be between about 0.05 mm and about 1 mm, between about 0.2 mm and about 0.8 mm, or between about 0.2 mm and about 0.5 mm. The wall thickness of the separation channels 302 can be between about 0.25 mm and about 2 mm, between about 0.5 mm and about 1.5 mm, or between about 1 mm and about 1.5 mm. The floor thickness of the separation channels 302 can be between about 0.2 mm and about 2 mm, between about 0.75 mm and about 1.75 mm, or between about 1 mm and about 1.25 mm. The roof thickness of the separation channels 302 can be between about 0.2 mm and about 2 mm, between about 0.75 mm and about 1.75 mm, or between about 1 mm and about 1.25 mm. The length of the separation channels 302 can be between about 10 mm and about 200 mm, between about 20 mm and about 150 mm, or between about 30 mm and about 100 mm. The flow rate through each of the separation channels can be between about 0.01 ml/min and about 1 ml/min, between about 0.1 ml/min and about 0.5 ml/min, or between about 0.1 ml/min and about 0.25 ml/min. The isolation slots 306 can have a width between about 0.05 mm and about 1.5 mm, between about 0.25 mm and about 1.5 mm, or between about 0.5 mm and about 1.25 mm.

The base substrate 308 of the microfluidic flow chamber 300 is an acoustically inactive substrate. For example, the base substrate 308 does not substantially transmit waves generated by the acoustic transducers 208. The acoustic transducers 208 and the heat sinks 312 are coupled to the base substrate 308. The base substrate 308 can also include electrical traces for powering the acoustic transducers 208. In some implementations, the base substrate 308, with its associated acoustic transducers 208 and heat sinks 312, is reusable and the microfluidic flow chamber 300 is disposable. A material of high thermal conductivity can be positioned between the acoustic transducers 208 and the base substrate 308. This material may be "heat sink compound", a thermally conducting grease, glycerol, graphite, or compressible sheets known as "gap pads" in the electronics industry.

As illustrated in FIG. 17, the acoustic transducers 208 are coupled to the right inner wall of the isolation slots 306. In the microfluidic flow chamber 300, each acoustic transducers 208 applies a standing wave 314 to the separation channel 302 to the right of the acoustic transducer 208. The standing wave 314 travels from the acoustic transducer 208, through the portion of the substrate 304 defining the left wall of the separation channel 302, into the separation channel 302, and then into the portion of the substrate 304 defining the right wall of the separation channel 302. As illustrated, the isolation slots 306 substantially fail to transmit the standing wave 314, which prevents the standing wave 314 from meaningfully effecting adjacent separation channels 302.

The microfluidic flow chamber 300 can be coupled to the base substrate 308 by glue or by mechanically coupling the microfluidic flow chamber 300 to the base substrate 308. For example, the microfluidic flow chamber 300 can be clamped to the base substrate 308. In some implementations, the base substrate 308 and the microfluidic flow chamber 300 include registration features that help properly position the substrate 304 on the base substrate 308. The microfluidic flow chamber 300 can be coupled to acoustic transducers 208 (or transducer) in a manner to substantially preserve uniform acoustic energy in each of the separation channels. The microfluidic flow chamber 300 can be coupled with the transducers 208 using an ultraviolet (UV) activated epoxy. The use of UV epoxy can enable accurate setup and positioning of the microfluidic flow chamber 300 in relation to the acoustic transducer before the UV epoxy is cured with UV light.

The heat sinks 312 of the microfluidic flow chamber 300 are configured to dissipate heat generated by the acoustic transducers 208. For example, the heat sinks 312 are configured to dissipate enough heat to prevent the acoustic transducers 208 from warming fluids flowing through the separation channels 302. In some implementations, the heat sinks 312 are, or include, thermoelectric coolers. In some implementations, the base substrate 308 includes fluidic lines that flow into the heat sinks 312 to provide fluidic cooling to the heat sinks 312.

Figure 19:
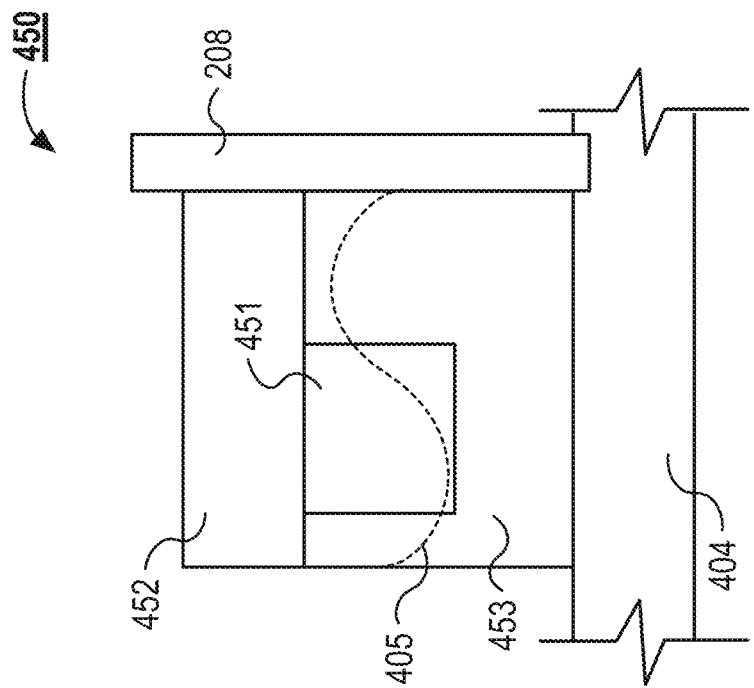
FIG. 19 illustrates a cross-sectional view of an example microfluidic flow chamber with asymmetrical walls as can be used in the system illustrated in FIG. 1.
Figure 18:
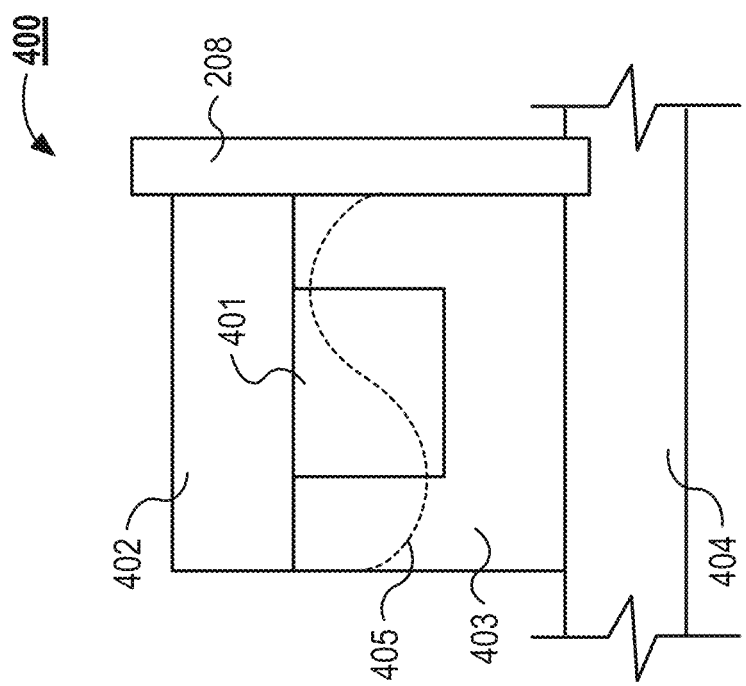
FIG. 18 illustrates a cross-sectional view of an example microfluidic flow chamber with symmetrical walls as can be used in the system illustrated in FIG. 1.

FIGS. 18 and 19 illustrate cross-sectional views of example microfluidic flow chambers. FIG. 18 illustrates a cross-sectional view of an example microfluidic flow chamber 400 with symmetrical walls, and FIG. 19 illustrates a cross-sectional view of an example microfluidic flow chamber 450 with asymmetrical walls. In some implementations, asymmetrical walls refer to opposite walls of the separation channels having different thicknesses. FIG. 18 illustrates a single separation channel 401, which may be one of an array of separation channels, as described above in relation to FIG. 13. The separation channel 401 is defined by a cover sheet 402 sitting atop a channel layer 403. The cover sheet 402 is coupled to the channel layer 403, which is coupled to a base substrate 404. As described above, an acoustic transducer 208 is coupled to an inner wall of a isolation slot and applies a standing wave 405 to the separation channel 401.

The channel layer 403 and cover sheet 402 of the separation channel 401 are manufactured from, and without limitation, polystyrene, glass and polyimide, polyacrylic, polysulfone, silicon, polystyrene, acrylic (polymethylmethacrylate), or other materials. In some implementations, the channel layer 403 is manufactured by milling, embossing, and/or etching. After creating the two layers, the two layers are joined together by thermocompression, mechanical clamping, adhesive bonding, and/or plasma bonding. The acoustic transducer 208 imparts the standing wave 405 at a specific wavelength (λ) across the separation channel 401. The dimensions of the channel layer 403, cover sheet 402, and separation channel 401 are dependent on the selected wavelength (λ), as described below.

As described above, in some implementations, the substrate sheet is relatively elastic (e.g., when a polystyrene or acrylic material is used), which provides a relatively lower acoustic contrast between the fluid flowing through the separation channel 401 and the walls of the channel layer 403. The relatively elastic materials can form a poor resonator. In implementations using relatively more elastic materials, the channel width can be defined using design rules and dimension ratios (with respect to the wall thickness, wave speed in the fluid and plastic, and/or the operating frequency) specific to plastics. For example, the channel width can be defined by a ratio of width of channel to width of wall, expressed as:

$$\frac{w_s}{w_f} = \frac{n}{2}\frac{c_s}{c_f}$$

$$n = 1, 2, 3, \ldots$$

which gives:

$$w_f \cong \lambda_f/4 = \frac{c_f}{4\omega}$$

The above dimensions can result in increased performance of driving particles to pressure nodes in separation channels constructed in thermoplastics. In the above equation, $c_f$ denotes acoustic velocity in the fluid flowing through the channel, $c_s$ denotes acoustic velocity in the wall material, the wall width is $w_s$, $w_f$ denotes the channel width, and $\lambda_f$ denotes the wavelength of the acoustic signal in the fluid.

In other implementations, where the material of the substrate is less elastic and forms a good acoustic resonator, the thickness of the side wall is equal to $c_{wall}/4f$, where $c_{wall}$ is the speed all of sound in the wall material. The $c_{wall}$ for the material is equal to the bulk longitudinal velocity of sound through the material $c_p$. In some implementations, odd multiples of the calculated wall thickness may be used. The width of the separation channel 401 is equal to about half the wavelength of the standing wave 405 in the fluid ($\lambda_{fluid}/2$).

In examples where the substrate is formed from a relatively more elastic material, the bulk longitudinal velocity of sound through the material $c_p$ is greater than the speed of sound through the fluid $c_{fluid}$, which is greater than speed of the reflected wave $c_s$. In these examples, the acoustic impedance mismatch between the shear wave and the longitudinal wave is small, which enables the standing wave 405 to be transferred from the channel layer 403 to the separation channel 401 with minimal loss of energy.

As an example and comparison between designs employing a weak resonator material and a strong resonator material, assume the substrate is formed from silicon and the separation channel is filled with water. In this example, assuming the speed of sound in water is about 1460 m/s and the acoustic transducer 208 is operated at about 1.7 MHz, the width of the separation channel would be about 0.4 mm and the wall thickness (based on a speed of sound in silicon of about 5968 m/s) would be 0.88 mm. When using a weak resonator material, such as polystyrene, the separation channel would be about 0.4 mm, but the wall thickness would be about 1.05 mm (based on a speed of sound in polystyrene of about 1120 m/s) and the transducer 208 is operated at about 1.0 MHz.

FIG. 19 illustrates a single separation channel 451, which may be one of an array of separation channels, as described above in relation to FIG. 13. The separation channel 451 is defined by a cover sheet 452 sitting atop a channel layer 453. The cover sheet 452 is coupled to the channel layer 453, which is coupled to a base substrate 404. As described above, an acoustic transducer 208 is coupled to an inner wall of an isolation slot and applies a standing wave 405 to the separation channel 451. As illustrated, the separation channel 451 is formed off-center with respect to the channel layer 453, which forms asymmetrically thick walls on either side of the separation channel 451. As illustrated, the thicker wall is adjacent to the acoustic transducer 208. In other implementations, the thinner wall can be adjacent to the acoustic transducer 208.

In some implementations, a microfluidic flow chamber with asymmetrical walls is formed in a substrate that has a relatively low acoustic impedance compared to the fluid flowing through the separation channels because it is important that the wave transfer between the wall material and fluid with relatively little energy loss. For example, the substrate is relatively more elastic (e.g., includes polystyrene or acrylic) than compared to silicon, glass, or a metal.

In some implementations, forming the microfluidic flow chamber 450 with asymmetrical walls enables the capture particles to be focused along an arbitrary axis of the separation channel 451. This is in contrast to implementations with symmetrical walls where the capture particles can be aligned with an axis in the center of the separation channel 401 or along the walls of the separation channel 401. In one example, the channel 451 dimensions and channel layer 453 width are calculated as described above with respect to the device with symmetrical walls, but one of the sidewalls is thicker than the other by a length equal to ¼ of the width of channel 451. In some implementations, the thicknesses of each of the walls is determined through numerical simulation.

In some implementations of the microfluidic flow chamber 450 with asymmetrical walls, the thicker wall has a thickness of about $c_w/4f+d$, and the thinner wall has a thickness of about $c_w/4f-d$. The lateral width of the separation channel is about $c_f/2f$. When calculating the thickness of the thicker and thinner wall $c_w$ is the acoustic velocity of an acoustic wave in the wall material (or an odd multiple thereof), $c_f$ is the acoustic velocity of the acoustic wave in the fluid, f is the desired operating frequency of the acoustic wave, and d is a width increment defined by $c_f/16f < d < c_f/4f$. In some implementations, f is multiplied by a factor of between about 1.5 and about 2.5, between about 1.5 and about 2, or about 1.7.

Figure 20:
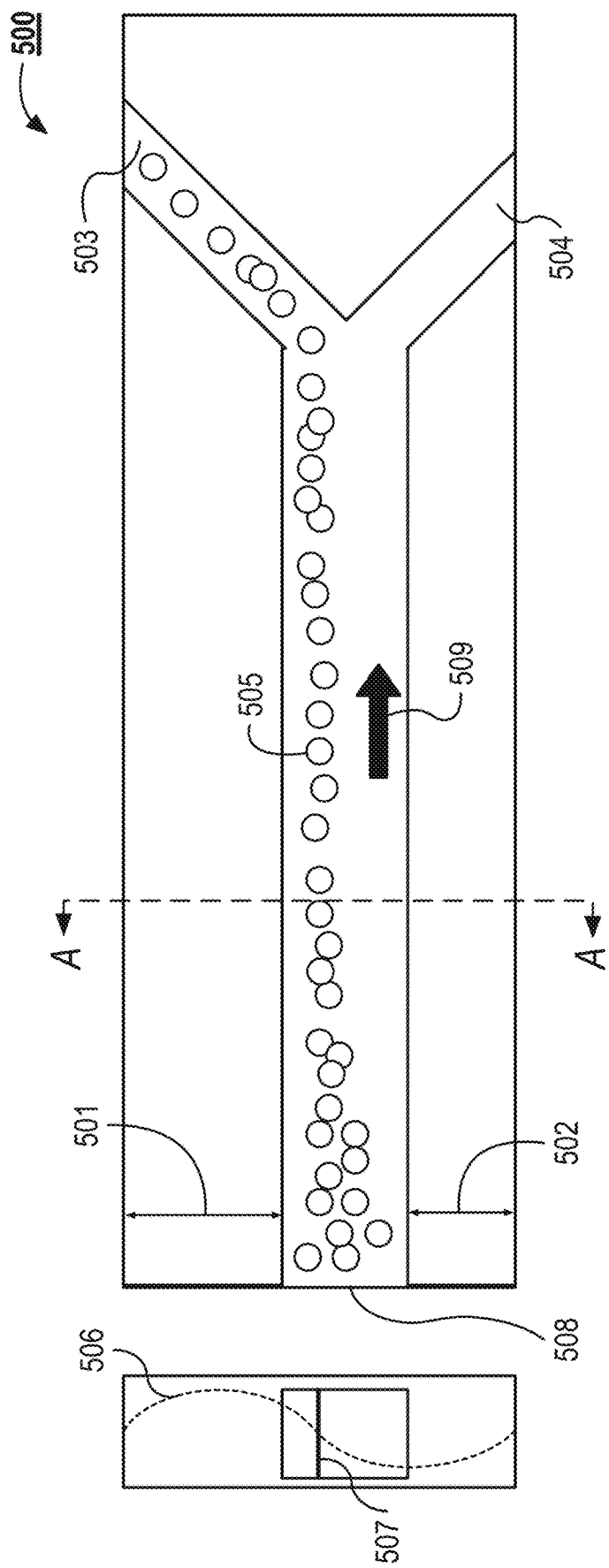
FIG. 20 illustrates a top view and cross-sectional view of an example microfluidic flow chamber with asymmetrical walls as can be used in the system illustrated in FIG. 1.

FIG. 20 illustrates a top view of an example separation channel 500 and a cross-sectional view of the separation channel 500 made along cut line A-A. The separation channel 500 includes asymmetrical walls, where wall 501 is thicker than wall 502. The separation channel 500 includes an inlet 508, a first outlet 503 and a second outlet 504. A plurality of capture particles 505 flow down the separation channel 500 in a direction 509 from the inlet 508 to the first and second outlets 503 and 504. A standing wave 506 is applied to the separation channel 500 forming an aggregation axis 507. In some implementations, the above described devices that include arrays of separation channels can include arrays of separation channels with asymmetrical walls.

The capture particles 505 align at the aggregation axis 507. The aggregation axis 507 can be formed at a pressure node or pressure antinode of the standing wave 506. As described in relation to FIG. 13, devices with symmetrical walls include three outlets to collect the separated contents of a fluid. For example, a device with symmetrical walls may align the capture particle toward the center of the separation channel. A capture particle dense fluid would then flow into a central outlet of the device, and a capture particle depleted fluid would slow into the two lateral outlets. However as described below in relation to FIG. 20, a device with asymmetrical walls, can be less complex because the separation channels can include only two outlets.

As illustrated in FIG. 20, using an asymmetrical wall design, the aggregation axis 507 is created between the central axis of the separation channel's lumen and the face of the wall 501 of the separation channel 500. As illustrated in FIG. 20, the aggregation axis 507 is generated toward the wall 501; however, the thicknesses of the walls 501 and 502 can be adjusted to place the aggregation axis 507 at any location in the separation channel 500. In this example, the capture particle dense fluid can be collected with a first outlet 503 and the capture particle depleted fluid is collected with the second outlet 504.

As illustrated, the first outlet 503 and the second outlet 504 are substantially the same size. In other implementations, the first outlet 503 and the second outlet 504 are sized differently. For example, the aggregation axis 507 can be placed closer to the wall 501, enabling the first outlet 503 to be smaller than the second outlet 504.

Figure 21:
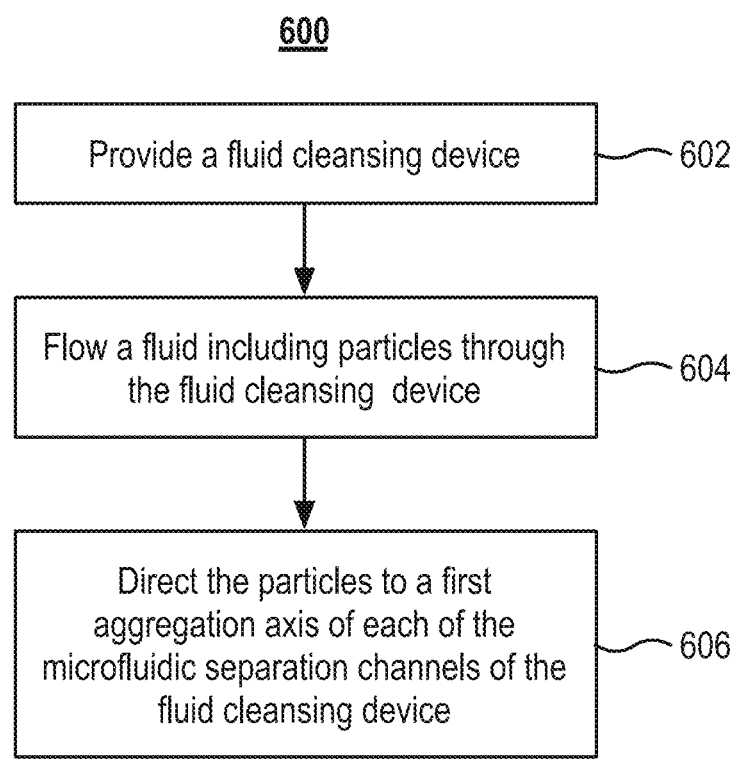
FIGS. 21 and 22 illustrates a flow chart of an example method of cleansing a fluid using the system illustrated in FIG. 1.

FIG. 21 illustrates a flow chart of an example method 600 of cleansing a fluid. The method 600 includes providing a fluid cleansing device (step 602). A fluid containing capture particles is flowed through the fluid cleansing device (step 604). The capture particles are directed toward a first aggregation axis in each of the separation channels of the fluid cleansing device (step 606).

As set forth above, the method 600 includes providing a fluid cleansing device (step 602). The fluid cleansing device can include any of the microfluidic flow chambers described herein. Also with reference to FIG. 13, the fluid cleansing device includes substrate 201 that defines an array of separation channels 202. Each of separation channels 202 includes an inlet 203 at an upstream portion and two or more outlets 204 at a downstream portion of the separation channel 202. Each of the adjacent separation channels 202 are separated from one another by an isolation slot 207. An acoustic transducer 208 is positioned within each of the isolation slots 207 and directs a standing acoustic wave toward a different one of the separation channels 202.

The method 600 also includes flowing a fluid through the fluid cleansing device (step 604). In some implementations, capture particles are mixed into the fluid before the fluid flows through the fluid cleansing device. The capture particles are configured to be acoustically mobile in the presence of a standing wave (e.g., the standing wave drives the capture particles to pressure node or pressure antinode). The acoustic mobility of the capture particles is tuned by configuring the capture particles to have a specific size, density, or compressibility. In some implementations, the capture particles are configured to be substantially more or substantially less acoustically mobile than other particles in the fluid. In some implementations, the capture particles include affinity particles anchored to the outer surface of the capture particles. The affinity particles are configured to bind to toxins, pro-inflammatory cytokines, bacteria, viruses, or specific cell types. In some implementations, cells, such as red blood cells, are acoustically mobile and may be driven to an aggregation axis without the use of capture particles.

The method 600 also includes directing the capture particles toward a first aggregation axis in each of the separation channels of the fluid cleansing device (step 606). Also with reference to FIGS. 13-20 and 3-temp11, each of the acoustic transducers 208 generate a standing acoustic wave within a respective separation channel. The standing waves forms pressure nodes and/or pressure antinodes within the separation channel, which form aggregation axis along the length of the separation channel. As illustrated in FIG. 20, the capture particles are directed toward the aggregation axis 507 by the standing wave 506. The aggregation axis 507 is aligned with the first outlet 503. As the fluid travels down the separation channel, the capture particles 505 align with the aggregation axis 507 and flow out the first outlet 503. Simultaneously, capture particles depleted fluid flows out the second outlet 504.

In an example where the capture particles include affinity particles that bind to a toxin, the capture particles can be mixed with a patient's blood. The capture particles will bind to the toxin in the patient's blood. As the capture particles flow down the separation channel, the capture particles, with their bound toxins, exit the fluid cleansing device at outlet 503. Blood substantially free of toxin exits the fluid cleansing device at outlet 504 and can be returned to the patient. In some implementations, the capture particles exiting the outlet 503 can be further processed to separate the capture particles (and toxins) from the blood flowing out the first outlet 503.

While the above method 600 is described in relation to cleaning a fluid, in some implementations, the method 600 can be used to enrich a fluid. For example, the capture particles may bind to desired particles (e.g., a specific type of cell), which can be directed toward an outlet and collected for further use.

Figure 22:
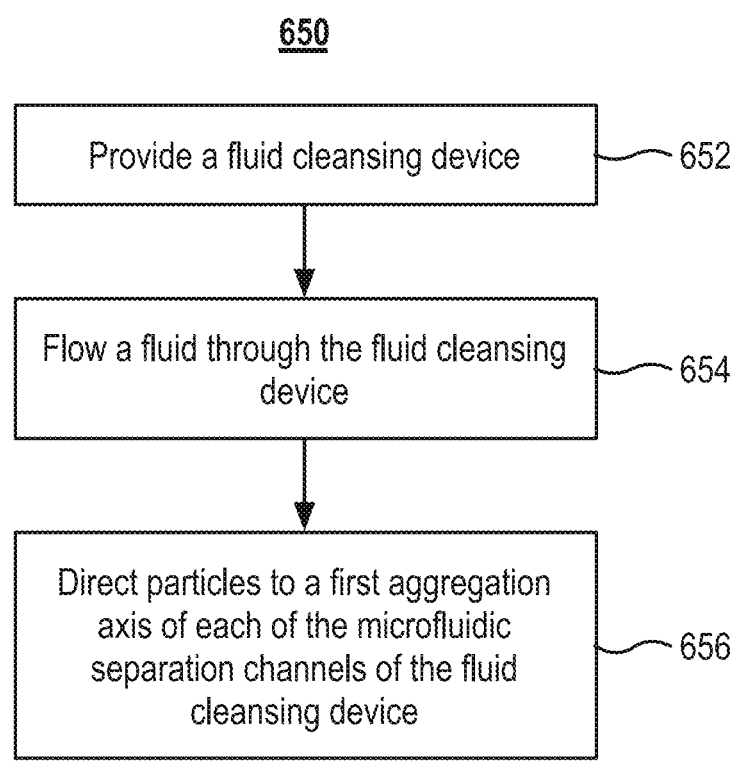

FIG. 22 illustrates a flow chart of an example method 650 for cleansing a fluid. The method 600 includes providing a fluid cleansing device (step 652). A fluid is flowed through the fluid cleansing device (step 654). Particles within the blood are directed toward a first aggregation axis in each of the separation channels of the fluid cleansing device (step 656).

As set forth above, the method 600 includes providing a fluid cleansing device (step 652). The fluid cleansing device can include any of the microfluidic flow chambers described herein. Also with reference to FIG. 13, the fluid cleansing device includes substrate 201 that defines an array of separation channels 202. Each of separation channels 202 includes an inlet 203 at an upstream portion and two or more outlets 204 at a downstream portion of the separation channel 202. Each of the adjacent separation channels 202 are separated from one another by an isolation slot 207. An acoustic transducer 208 is positioned within each of the isolation slots 207 and directs a standing acoustic wave toward a different one of the separation channels 202.

The method 650 also includes flowing a fluid through the fluid cleansing device (step 654). The fluid can be blood. Some particles within the fluid, such as red blood cells, cells, or other elements within the fluid, can be acoustically mobile in the presence of a standing wave (e.g., the standing wave drives the particles to pressure node or pressure antinode).

The method 650 also includes directing the particles of the fluid toward a first aggregation axis in each of the separation channels of the fluid cleansing device (step 656). Also with reference to FIGS. 13-20 and 3-temp11, each of the acoustic transducers 208 generate a standing acoustic wave within a respective separation channel. The standing waves forms pressure nodes and/or pressure antinodes within the separation channel, which form aggregation axis along the length of the separation channel. As illustrated in FIG. 20, the particles in the fluid (e.g., red blood cells) are directed toward the aggregation axis 507 by the standing wave 506. The aggregation axis 507 is aligned with the first outlet 503. As the fluid travels down the separation channel, the particles align with the aggregation axis 507 and flow out the first outlet 503. Simultaneously, particles depleted fluid (e.g., fluid without red blood cells) flows out the second outlet 504.

The disclosed system and methods may be embodied in other specific forms without departing from the spirit or essential characteristics thereof. The forgoing implementations are therefore to be considered in all respects illustrative, rather than limiting of the invention.

The invention claimed is:

1. A separation device comprising:
  a first substrate comprising:
    a first plurality of microfluidic channels defined in a first face of the first substrate, wherein each of the first plurality of microfluidic channels comprises an upstream portion and a downstream portion;
    a second plurality of microfluidic channels defined in a second face of the first substrate, wherein each of the second plurality of microfluidic channels comprises an upstream portion and a downstream portion; and
    a plurality of connecting channels coupling the downstream portion of the first plurality of microfluidic channels to the upstream portion of the second plurality of microfluidic fluid channels;

a second substrate coupled with the first face of the first substrate, the second substrate defining a wall of the first plurality of microfluidic fluid channels; and a third substrate coupled with the second face of the first substrate, the third substrate defining a wall of the second plurality of microfluidic fluid channels, wherein at least one of the first substrate, the second substrate, and the third substrate is configured to couple with a base substrate comprising one or more acoustic transducers.

2. The separation device of claim 1, wherein the first substrate comprises an isolation slot positioned between each of the first plurality of microfluidic fluid channels.

3. The separation device of claim 2, wherein each of the one or more acoustic transducers protrudes perpendicular to a face of the base substrate and into the isolation slot positioned between each of the first plurality of microfluidic fluid channels.

4. The separation device of claim 2, wherein the isolation slot positioned between each of the first plurality of microfluidic fluid channels runs substantially parallel to and an entire length of the first plurality of microfluidic channels.

5. The separation device of claim 1, further comprising the base substrate comprising the one or more acoustic transducers, each of the one or more acoustic transducers coupled with the second face of the first substrate.

6. The separation device of claim 1, wherein the downstream portion of the each of the first plurality of microfluidic fluid channels further comprises a first outlet positioned substantially along a longitudinal axis.

7. The separation device of claim 1, wherein the downstream portion of the each of the first plurality of microfluidic fluid channels further comprises a second outlet positioned adjacent to a lateral wall of a first outlet positioned substantially along a longitudinal axis.

8. The separation device of claim 1, wherein the first substrate defines a manifold configured to distribute a fluid to the first plurality of microfluidic fluid channels.

9. The separation device of claim 8, wherein the manifold comprises a network of biomimetic channels.

10. The separation device of claim 8, wherein a distribution portion of the manifold is defined in the first face of the first substrate and a collection portion of the manifold is defined in the first face and the second face of the first substrate.

11. The separation device of claim 10, wherein a portion of the collection portion of the manifold defined in the second face of the first substrate is fluidically connected to the collection portion of the manifold defined in the first face of the first substrate by the plurality of connecting channels.

12. The separation device of claim 1, wherein each of the first plurality of microfluidic channels further comprise:
a first wall having a first thickness; and
a second wall opposite the first wall and having a second thickness.

13. The separation device of claim 12, wherein the second thickness is different than the first thickness.

14. A method comprising:
providing a fluid cleansing device comprising:
a first substrate comprising:
a first plurality of microfluidic channels defined in a first face of the first substrate, wherein each of the first plurality of microfluidic channels comprises an upstream portion and a downstream portion;
a second plurality of microfluidic channels defined in a second face of the first substrate, wherein each of the second plurality of microfluidic channels comprises an upstream portion and a downstream portion; and
a plurality of connecting channels coupling the downstream portion of the first plurality of microfluidic channels to the upstream portion of the second plurality of microfluidic fluid channels;
a second substrate coupled with the first face of the first substrate, the second substrate defining a wall of the first plurality of microfluidic fluid channels; and
a third substrate coupled with the second face of the first substrate, the third substrate defining a wall of the second plurality of microfluidic fluid channels, wherein at least one of the first substrate, the second substrate, or the third substrate is configured to couple with a base substrate comprising one or more acoustic transducers;
flowing a fluid comprising particles through the first plurality of microfluidic channels; and
directing, with an acoustic wave generated by the one or more acoustic transducers, the particles to a first aggregation axis of each of the first plurality of microfluidic channels.

15. The method of claim 14, further comprising flowing the fluid through a manifold defined in the first substrate.

16. The method of claim 15, wherein the manifold comprises a network of biomimetic channels.

17. The method of claim 15, further comprising:
flowing the fluid through a distribution portion of the manifold defined in the first face of the first substrate; and
collecting at least a portion of the fluid at a collection portion of the manifold defined in the first face and the second face of the first substrate.

18. The method of claim 14, wherein the first substrate comprises an isolation slot positioned between each of the first plurality of microfluidic fluid channels.

19. The method of claim 18, wherein each of the one or more acoustic transducers protrudes perpendicular to a face of the base substrate and into the isolation slot positioned between each of the first plurality of microfluidic fluid channels.

20. The method of claim 14, further comprising selecting a frequency of the acoustic wave based on a wall thickness of the first substrate.

* * * * *